United States Patent
Yang et al.

(10) Patent No.: US 12,383,141 B2
(45) Date of Patent: Aug. 12, 2025

(54) PHOTOACOUSTIC AND ULTRASONIC ENDOSCOPY SYSTEM INCLUDING A COAXIALLY CONFIGURED OPTICAL AND ELECTROMAGNETIC ROTARY WAVEGUIDE ASSEMBLY AND IMPLEMENTATION METHOD THEREOF

(71) Applicant: UNIST(ULSAN NATIONAL INSTITUTE OF SCIENCE AND TECHNOLOGY), Ulsan (KR)

(72) Inventors: Joon-Mo Yang, Daejeon (KR); Chae Un Kim, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 178 days.

(21) Appl. No.: 17/592,436

(22) Filed: Feb. 3, 2022

(65) Prior Publication Data
US 2022/0151469 A1    May 19, 2022

Related U.S. Application Data

(63) Continuation of application No. 15/645,969, filed on Jul. 10, 2017, now Pat. No. 11,272,831.

(30) Foreign Application Priority Data

Aug. 24, 2016    (KR) .......................... 10-2016-0107773

(51) Int. Cl.
*A61B 5/00*    (2006.01)
*A61B 1/00*    (2006.01)
(Continued)

(52) U.S. Cl.
CPC ........ *A61B 5/0066* (2013.01); *A61B 1/00117* (2013.01); *A61B 1/04* (2013.01);
(Continued)

(58) Field of Classification Search
CPC ..... A61B 5/0066; A61B 1/00117; A61B 1/04; A61B 5/0035; A61B 5/0095;
(Continued)

(56) References Cited

U.S. PATENT DOCUMENTS 3,845,375 A    10/1974    Stiebel
4,857,046 A    8/1989    Stevens et al.
(Continued)

FOREIGN PATENT DOCUMENTS

JP    2009-183416 A    8/2009
JP    2011-072401 A    4/2011
(Continued)

OTHER PUBLICATIONS

"Sliding Ring Seal." Sliding Ring Seal—HAWE North America, www.hawe.com/en-us/fluid-lexicon/sliding-ring-seal/ (Year: 2025).*

*Primary Examiner* — Joel Lamprecht
*Assistant Examiner* — Amy Shafqat
(74) *Attorney, Agent, or Firm* — Klarquist Sparkman, LLP

(57) ABSTRACT

A photoacoustic-ultrasonic dual-mode endoscope includes: a probe and a probe driving unit, wherein the probe includes: a coaxially configured optical and electromagnetic rotary waveguide assembly including an optical fiber, the optical fiber including a core and a cladding, and a conductive path coaxially arranged with the optical fiber; a scanning tip located at an end of the coaxially configured optical and electromagnetic rotary waveguide assembly and configured to deliver a laser beam to an object to be examined and detect a photoacoustic signal and an ultrasonic signal generated from the object to be examined; and a plastic catheter surrounding outer surfaces of the coaxially configured optical and electromagnetic rotary waveguide assembly and the scanning tip, wherein the conductive path includes: a first (Continued)

conductive path including a portion coaxially arranged with the optical fiber; and a second conductive path including a portion coaxially arranged with the optical fiber and insulated from the first conductive path.

15 Claims, 14 Drawing Sheets

(51) Int. Cl.
A61B 1/04 (2006.01)
A61B 8/00 (2006.01)
A61B 8/12 (2006.01)

(52) U.S. Cl.
CPC .......... *A61B 5/0035* (2013.01); *A61B 5/0095* (2013.01); *A61B 5/6852* (2013.01); *A61B 8/12* (2013.01); *A61B 8/4416* (2013.01); *A61B 8/445* (2013.01); *A61B 1/00165* (2013.01); *A61B 8/4461* (2013.01); *A61B 2562/247* (2013.01)

(58) Field of Classification Search
CPC ....... A61B 5/6852; A61B 8/12; A61B 8/4416; A61B 8/445; A61B 1/00165; A61B 8/4461; A61B 2562/247; A61B 8/4444
See application file for complete search history.

(56) References Cited

U.S. PATENT DOCUMENTS

| | | | |
|---|---|---|---|
| 4,951,677 A | 8/1990 | Crowley et al. | |
| 4,979,939 A | 12/1990 | Shiber | |
| 5,421,338 A | 6/1995 | Crowley et al. | |
| 5,486,170 A | 1/1996 | Winston et al. | |
| 5,503,155 A | 4/1996 | Salmon et al. | |
| 6,004,269 A | 12/1999 | Crowley et al. | |
| 6,027,460 A | 2/2000 | Shturman | |
| 6,134,003 A | 10/2000 | Tearney et al. | |
| 6,137,621 A | 10/2000 | Wu | |
| 6,261,246 B1 | 7/2001 | Pantages et al. | |
| 6,454,717 B1 | 9/2002 | Pantages et al. | |
| 6,559,437 B1 | 5/2003 | Pope, Jr. et al. | |
| 6,982,384 B2 | 1/2006 | Hall et al. | |
| 7,663,293 B2 | 2/2010 | Sohn et al. | |
| 7,952,718 B2 | 5/2011 | Li et al. | |
| 7,998,157 B2 | 8/2011 | Culp et al. | |
| 8,104,479 B2* | 1/2012 | Glynn ................. A61B 8/4422 128/853 |
| 8,169,618 B2 | 5/2012 | Inoue | |
| 8,183,872 B2 | 5/2012 | Stark | |
| 8,220,688 B2 | 7/2012 | Laurent et al. | |
| 8,493,224 B2 | 7/2013 | Coon | |
| 8,568,425 B2 | 10/2013 | Ross et al. | |
| 8,721,631 B2 | 5/2014 | Neuberger | |
| 8,997,792 B2 | 4/2015 | Betsinger et al. | |
| 9,036,966 B2 | 5/2015 | Bhagavatula et al. | |
| 9,069,122 B2 | 6/2015 | Takeuchi et al. | |
| 9,125,562 B2 | 9/2015 | Spencer et al. | |
| 9,186,209 B2 | 11/2015 | Weber et al. | |
| 9,360,630 B2 | 6/2016 | Jenner et al. | |
| 9,387,305 B2 | 7/2016 | Courtney et al. | |
| 9,394,896 B2 | 7/2016 | Dunn et al. | |
| 9,414,738 B2 | 8/2016 | Huszar et al. | |
| 9,488,782 B2 | 11/2016 | Griffin | |
| 9,492,651 B2 | 11/2016 | Bottomley et al. | |
| 9,539,008 B2 | 1/2017 | Pribanic et al. | |
| 9,549,663 B2 | 1/2017 | Larkin | |
| 9,574,870 B2 | 2/2017 | Yamazaki et al. | |
| 9,603,547 B2* | 3/2017 | Stigall ................. A61B 8/0891 |
| 9,763,741 B2 | 9/2017 | Alvarez et al. | |
| 9,869,821 B2 | 1/2018 | Yamazaki et al. | |
| 9,901,342 B2 | 2/2018 | Shelton, IV et al. | |
| 10,595,820 B2 | 3/2020 | Stigall et al. | |
| 10,765,425 B2 | 9/2020 | Yates et al. | |
| 2005/0165315 A1 | 7/2005 | Zuluaga et al. | |
| 2006/0001863 A1 | 1/2006 | Kishida et al. | |
| 2007/0179485 A1 | 8/2007 | Yeik et al. | |
| 2007/0233396 A1 | 10/2007 | Tearney et al. | |
| 2009/0166478 A1 | 7/2009 | Choi | |
| 2009/0198125 A1 | 8/2009 | Nakabayashi et al. | |
| 2010/0292533 A1 | 11/2010 | Kasahara et al. | |
| 2011/0054507 A1 | 3/2011 | Batten et al. | |
| 2011/0077463 A1 | 3/2011 | Hirota | |
| 2011/0206838 A1 | 8/2011 | Juni et al. | |
| 2011/0213391 A1 | 9/2011 | Rivers et al. | |
| 2012/0004710 A1 | 1/2012 | Kerber | |
| 2012/0071752 A1 | 3/2012 | Sewell et al. | |
| 2012/0245457 A1 | 9/2012 | Crowley | |
| 2012/0253340 A1 | 10/2012 | Stevenson et al. | |
| 2013/0023770 A1 | 1/2013 | Courtney et al. | |
| 2013/0079810 A1* | 3/2013 | Isenberg ............ A61B 18/1447 606/205 |
| 2013/0211433 A1 | 8/2013 | Kadykowski et al. | |
| 2013/0338498 A1 | 12/2013 | Emelianov et al. | |
| 2015/0257704 A1 | 9/2015 | Courtney | |
| 2015/0257783 A1 | 9/2015 | Levine et al. | |
| 2015/0305708 A1 | 10/2015 | Stigall et al. | |
| 2016/0290835 A1 | 10/2016 | McCoy | |
| 2016/0374562 A1 | 12/2016 | Vertikov | |
| 2017/0235126 A1 | 8/2017 | DiDomenico | |
| 2019/0374196 A1* | 12/2019 | Courtney ............. A61B 5/0066 |
| 2024/0074731 A1* | 3/2024 | Leblanc ................. A61B 8/12 |

FOREIGN PATENT DOCUMENTS

| | | |
|---|---|---|
| JP | 2013-027482 A | 2/2013 |
| JP | 2014-518717 A | 8/2014 |
| JP | 2016-093366 A | 5/2016 |

* cited by examiner

PHOTOACOUSTIC AND ULTRASONIC ENDOSCOPY SYSTEM INCLUDING A COAXIALLY CONFIGURED OPTICAL AND ELECTROMAGNETIC ROTARY WAVEGUIDE ASSEMBLY AND IMPLEMENTATION METHOD THEREOF

CROSS-REFERENCE TO RELATED APPLICATION

This application is a continuation of U.S. patent application Ser. No. 15/645,969, filed Jul. 10, 2017, which claims the benefit of Korean Patent Application No. 10-2016-0107773, filed on Aug. 24, 2016, in the Korean Intellectual Property Office, the disclosures of which are incorporated herein in their entirety by reference.

BACKGROUND

1. Field

One or more of the embodiments described in the present disclosure relate to a medical tomographic endoscopic apparatus that has a long and slender probe shape, like the current endoscopic ultrasound (EUS) probes utilized in clinics, wherein the endoscopic apparatus is inserted into the object to be examined and provides a tomographic image of the interior thereof. The key feature of the proposed endoscopic system is the ability to provide both a high-quality photoacoustic image and a typical ultrasonic endoscopic image based on the improved probe flexibility and rotational uniformity compared to existing photoacoustic endoscopic systems. The inventive concept of the present disclosure may be applied to various medical imaging applications, such as the diagnosis of a digestive disease or cardiovascular disease.

2. Description of the Related Art

The present disclosure relates to a range of tomographic endoscopic systems that can provide cross-sectional or volumetric images of target tissue according to the general principle of photoacoustic endoscopy (PAE) and EUS by consolidating the relevant functions in a single device. The proposed endoscopic systems are intended to be used for such medical procedures as the diagnosis of a digestive disease or cardiovascular disease by using a method similar to that of an EUS mini-probe or an intravascular ultrasound (IVUS) catheter probe, both of which are currently utilized in clinics.

The general principle of EUS is already well known, well established, and currently being utilized. However, PAE refers to the novel tomographic endoscopic technique that embodies the photoacoustic imaging technique in a small probe. In an illustrative imaging procedure, a probe with a small diameter is inserted into an object to be examined. Electromagnetic waves with a very short pulse width (usually less than 1 µs) are instantly applied to the region of interest to generate acoustic waves, which are typically referred to as photoacoustic waves, and a tomographic image of the interior of the biological tissue is produced by obtaining (i.e., scanning) the generated photoacoustic signals over the region of interest.

Although the photoacoustic effect through which electromagnetic waves are applied to a target object and converted into acoustic waves has been known since the 1880s, it was not until the early of 1990s that the first photoacoustic image was actually obtained from real biological tissue based on the photoacoustic effect. At that time, the advent of commercial pulsed-light sources, such as the Q-switched laser, played a crucial role in the breakthrough; from then on, various types of photoacoustic imaging systems have been developed with a greater range of medical applicability. In general, a technique that can provide a tomographic image of the interior of biological tissue based on the photoacoustic effect is referred to as photoacoustic imaging (PAI) or photoacoustic tomography (PAT) in a broader sense.

The reason that PAT is currently in the medical imaging spotlight is because it is capable of providing a new type of medically useful image information that is not possible with conventional medical imaging techniques, such as magnetic resonance imaging, X-ray computed tomography, positron emission tomography, and ultrasound imaging. Also, it is widely accepted that PAT is very superior in terms of the imaging depth, spatial resolution, imaging speed, and safety, all of which are critical factors for real clinical use. In short, the present disclosure relates to the endoscopic application of PAT, and it is intended to provide a description of the apparatus, the operation of the apparatus, and a method for implementing the apparatus that may solve the problems related to existing PAE systems.

Like more well-known or more general PAT systems (that are not limited to endoscopy), a PAE system also requires three core system elements: a light source that generates an electromagnetic pulse, an imaging probe that approaches an object to be examined and acquires a series of photoacoustic signals, and a data processor and displayer that process the acquired photoacoustic signals and provide the processed photoacoustic image to a user. However, the most important and distinguishable technical requirement for the specific application of endoscopy is an imaging probe with a very small or slender and long form.

After the first conceptual suggestion of PAE by Oraevsky et al. in 1997 as described in Prior Document 5, in which the imaging probe was referred to as optoacoustic endoscope (OAE), a number of PAE probes were developed to address such technical requirements as "probe miniaturization" and "specifying a device configuration or operation principle for endoscopy." However, no commercially successful or clinically applicable PAE system that satisfies both of the technical requirements has been developed yet due to many underlying technical challenges. The most well-known and toughest challenge is that to successfully create a working PAE probe, all the optical and acoustic elements should be effectively integrated and arranged in a small and restricted space; an adequate scanning mechanism, through which a tomographic image can be produced, should also be developed and integrated into the device. Accordingly, the main purpose of the present disclosure is to provide an advanced PAE system concept that may allow an imaging probe to be inserted into the living object to be examined and provide a photoacoustic signal to obtain an image more effectively than in prior attempts.

Although there is a clear difference between the principles of PAE and EUS, in which a PAE image is produced through the unique energy transduction mechanism that converts pulsed electromagnetic waves into acoustic waves, PAE is still very closely related to conventional EUS. This is because all of the signals required to produce a PAE image are acquired by means of acoustic waves. This means that, in some respects, a PAE device can be understood as a device in which the functions that guide and emit laser light or electromagnetic waves are added to the typical system composition of a conventional EUS device. Due to these system characteristics, most PAE systems may be able to provide both a photoacoustic and a typical ultrasound image.

Hence, regarding methods of ultrasound signal detection other than those that deliver and emit electromagnetic waves (e.g., a laser beam in general) to an object to be examined, any of the single-element ultrasonic transducer-based mechanical scanning mechanism or array transducer-based electronic scanning mechanism currently being utilized in clinical EUS instruments may also be utilized in a PAE probe. The advantages and disadvantages of the mechanical and the electronic scanning mechanisms will be briefly explained in the following.

First, the main advantage of the electronic scanning mechanism is that all of the one-dimensional signals (i.e., A-lines) needed to produce a two-dimensional (2D) or three-dimensional (3D) tomographic image may be simultaneously obtained through the plurality of detection channels formed in an array transducer by using a single shot of an electromagnetic pulse (e.g., laser puke). This means that, without making any changes to the sensor or probe position, a tomographic image covering a certain range of the target region may be acquired at one time after just one laser puke firing. However, the main drawback of the electronic scanning mechanism is that, since it is relatively more difficult to reduce the size of the related endoscopic probe than that of the mechanical scanning mechanism, such problems as crosstalk or signal interference between channels may occur; the costs of implementing the system may also be high. Due to the aforementioned problems with an array transducer, in the current EUS technology utilized in clinics, the electronic scanning mechanism is mostly adopted to such EUS devices that are manufactured for the diagnosis of digestive diseases, for which high-level miniaturization is unnecessary (of course, an EUS instrument does not require a laser pulse guiding and emitting function).

In contrast, the mechanical scanning mechanism differs from the electronic scanning mechanism in the following ways. First, its major drawback is that, since a single-element ultrasonic transducer that can receive the signals bounced back only from the aiming direction of the transducer surface is mounted on the scanning tip of an endoscopic probe, in order to obtain a 2D or 3D image, a series of processes that emit a laser pulse and then detect the generated photoacoustic waves should be repeatedly performed by changing the physical position or the aiming direction of the ultrasonic transducer (e.g., rotational scanning in general). However, the mechanical scanning mechanism also has advantages. Since the space occupied by the single transducer is not so large, forming a very small or slender-shaped probe may be possible. The costs of developing and creating the instrument are also relatively low. Accordingly, in the current EUS technology utilized in clinics, the mechanical scanning mechanism is mostly applied to ultra-small endoscopic instruments with probe diameters ranging from ~1 mm to ~3 mm, such as IVUS catheter probes manufactured for introduction into blood vessels or EUS mini-probes manufactured to be inserted into the instrument channels or the accessory channels of a video endoscope.

Due to the aforementioned advantages and disadvantages, various PAE systems with the adoption of one of the two ultrasound signal detection mechanisms have been suggested so far. Among them, representative examples of prior technologies using a single-element ultrasonic transducer-based mechanical scanning mechanism, which is actually the same mechanism that the present disclosure has also adopted as a technical basis, include Prior Document 1 (US Patent Application Publication No. 2011-0021924), Prior Document 2 (US Patent Application Publication No. 2011-0275890), Prior Document 3 (Journal of Biomedical Optics 19(6), 066001(2014)), and Prior Document 4 (PLOS ONE 9(3), e92463 (2014)).

The endoscopic systems disclosed in the four prior documents mentioned above use a mechanical scanning mechanism in which a light illumination unit coupled to the end of an optical fiber to deliver laser light and a single-element ultrasonic transducer to detect generated photoacoustic waves are closely placed at the scanning tip of a probe; signal data to produce a photoacoustic image is acquired through the predetermined rotational motion of the scanning tip. However, the methods of placing the optical fiber, the light illumination unit, and the ultrasonic transducer, as well as a detailed scanning mechanism to obtain an image based on the aforementioned system configuration differ among the endoscopic systems disclosed in the prior documents. These differences will be briefly reviewed and discussed.

First, in the PAE probe disclosed in Prior Document 1, a single-element ultrasonic transducer is placed at the scanning tip, like an existing ultrasound-based IVUS catheter probe. The mechanical torque required for the rotational motion of the scanning tip is transmitted from the proximal part of the system to the scanning tip through a mechanical component called a "torque coil" (in the drawing, it seems that a real commercial IVUS catheter or its equivalent is directly placed at the central part of the endoscopic probe to realize the mentioned parts and function). However, the most notable feature of the endoscopic probe is that a plurality of optical fibers to deliver laser light are placed at predetermined intervals around the IVUS catheter or its equivalent so that the required process for photoacoustic imaging can be performed. In this configuration, the main advantage is that the optical fibers are placed around the catheter, which is typically a plastic tube, and may be statically connected to the proximal part of the endoscopic probe, whereas the ultrasonic transducer is located at the central part of the endoscopic probe and rotates inside the plastic catheter. However, the main drawback of the endoscopic configuration may be that, since the multiple optical fibers are placed around the IVUS catheter, the flexibility of the probe may significantly deteriorate. The intensity of the laser light irradiated to the target tissue may also not be uniform over the 360-degree rotational angle.

In contrast, the endoscopic systems disclosed in Prior Documents 2 through 4 do not have the above problems and have features as follows.

The most prominent feature and the biggest advantage of the endoscopic system disclosed in Prior Document 2 is a scanning mirror that can reflect both laser light and acoustic waves; it can also physically rotate and is employed inside the scanning head of the endoscopic probe. Both the signal wire of the transducer and the optical fiber that delivers the laser light can therefore be statically connected to the proximal part of the endoscopic probe along the probe body. However, the endoscopic system also has problematic issues. Since an actuator for driving the scanning mirror has to be mounted inside the scanning head of the probe, the flexibility of the distal section may be greatly reduced (in fact, this reduction in the flexibility runs counter to the original objective of such a mini-probe and may cause many problems when the endoscopic system is used in real clinics).

On the other hand, the endoscopic system disclosed in Prior Document 3, which may be regarded as an alternative embodiment derived from the basic concept of Prior Document 2, differs in the following ways. Only a single strand of optical fiber placed inside a torque coil along the central axis of the endoscopic probe performs a rotational scanning along with a scanning mirror, whereas an ultrasonic transducer and its signal wire are still statically connected from the scanning head to the proximal part of the endoscopic probe along the outer surface of a plastic tube or catheter. So, when the endoscopic system concept described in Prior Document 3 is used, the total length of the rigid distal section of the endoscopic probe may be formed with a much shorter length than that of the endoscopic system described in Prior Document 2. However, the endoscopic system in Prior Document 3 has the problem that a portion of the angular field-of-view is inevitably blocked by the signal wire of the transducer (i.e., a blind spot is formed in the image), and the probe has an asymmetrical structure due to the signal wire. Thus, the rotation speed of the scanning tip may not be uniform when the rotational scanning is performed with the probe bent into a complex shape.

In these respects, the endoscopic system described in Prior Document 4 displays many interesting system features that may be able to solve most of the above problems. First, regarding structure, a light illumination unit and an ultrasonic transducer element with a small size are placed together in the scanning tip which is formed at the distal end of the probe. A signal wire to transmit electrical signals from the transducer as well as an optical fiber to deliver a laser beam to the light illumination unit are installed in a flexible and tubular coil, which is referred to as a flexible shaft or a torque coil; these perform a rotational scanning along with the scanning tip. In this case, the torque coil that encloses the signal wire and the optical fiber acts as the key mechanically-rotating agent that transmits the mechanical torque supplied from a proximal part of the endoscopic probe to the scanning tip (in the endoscopy field, the related operational principle is referred to as a torque coil-based proximal actuation mechanism).

In fact, a method of implementing a PAE probe like the endoscopic system described in Prior Document 4, in which a single-element ultrasonic transducer and a single strand of optical fiber are employed and the signal wire of the transducer and the optical fiber are placed very closely in parallel by forming a long probe structure, was first suggested in Prior Document 5 published in 1997. Afterward, the same or similar design concepts with minor variations have been continuously applied to later PAE systems (e.g., Prior Documents 6, 7, and 8). Also, a method of transmitting mechanical torque from the proximal part of an endoscopic system to a scanning tip via a torque coil, thus performing a rotational scanning, has also been continuously applied to many EUS mini-probes or endoscopic optical coherence tomography (OCT) probes (e.g., Prior Documents 9 and 10) for more than twenty years.

In this regard, a PAE system that employs a torque coil-based proximal actuation mechanism may be understood as a photoacoustic version of an EUS mini-probe because all current clinical EUS mini-probes are also operated based on the same scanning mechanism. However, the biggest difference between the PAE probe and the EUS mini-probe is that an optical fiber to deliver laser light is additionally required for the PAE imaging function, and it should be properly installed somewhere inside a torque coil. In addition, another very important system component capable of transmitting and/or receiving both laser light and transducer electrical signals without interference should be embodied effectively at the proximal part of a PAE probe. In other words, if the torque coil-based proximal actuation mechanism is adopted for a PAE system, as in the case of Prior Document 4, the development of a rotary optical and electromagnetic coupling unit (or the like) with a more complicated structure than that of an existing EUS mini-probe would be one of the key tasks.

Nonetheless, the achievement of a PAE system based on the aforementioned torque coil-based proximal actuation mechanism is still regarded as one of the ultimate goals in the related field because the mechanism has a key advantage: the entire catheter section of an endoscopic probe may be formed with much greater flexibility than in the endoscopic systems described in Prior Documents 1 through 3. Besides, the mechanism also enables full 360-degree rotational scanning without including any blind spot in an acquired image.

As the probe flexibility is a primary consideration in designing an EUS mini-probe with the main objective of being inserted into the instrument channel of a video endoscope or an IVUS catheter probe with the main objective of diagnosing the interior of a blood vessel that is physically very weak, so far a number of PAE systems (e.g., in Prior documents 4 and 8) have been developed that are based not only on the scanning mechanism of the EUS mini-probe or the IVUS catheter probe, but also on the application objects and the probe types similar to the EUS mini-probe or the IVUS catheter probe, which actually use the same torque coil-based proximal actuation mechanism. However, none of the prior documents have described a successfully achieved PAE system with the torque coil-based proximal actuation mechanism.

PRIOR DOCUMENTS

Patent Documents

Prior Document 1: US Patent Application Publication No. 2011-0021924 (Jan. 27, 2011)
Prior Document 2: US Patent Application Publication No. 2011-0275890 (Nov. 10, 2011)
Prior Document 7: US Patent Application Publication No. 2011-0098572 (Apr. 28, 2011)
Prior Document 10: U.S. Pat. No. 6,134,003 (Oct. 17, 2000)

Non-Patent Documents

Prior Document 3: J M Yang, et al., "Catheter based photoacoustic endoscope", Journal of Biomedical Optics 19(6), 066001 (2014)
Prior Document 4: X Bai, et al., "Intravascular optical-resolution photoacoustic tomography with a 1.1 mm diameter catheter", PLOS ONE 9(3), e92463 (2014)
Prior Document 5: Oraevsky, et al., Proc. SPIE, 2979, 59 (1997)
Prior Document 6: Viator, et al., "Design and testing of an endoscopic photoacoustic probe for determination of treatment depth after photodynamic therapy", Proc. SPIE 4256, 16-27 (2001)
Prior Document 8: Da Xing, et al., "Characterization of lipid-rich aortic plaques by intravascular photoacoustic tomography", Journal of the American college of cardiology 64(4), 385-390 (2014)
Prior Document 9: G. J. Tearney, et al., "Scanning single-mode fiber optic cateter-endoscope for optical coherence tomography", Optics Letters 21(7), 543-545 (1996)
Prior Document 11: J M Yang, et al., "Simultaneous functional photoacoustic and ultrasonic endoscopy of internal organs in vivo," Nature Medicine 18(8), 1297 (2012).

SUMMARY

Existing PAE systems (e.g., in Prior Documents 4, 7, and 8) using a torque coil-based proximal actuation mechanism have problems in that, since the optical fiber and the signal wire are simply arranged in a parallel structure inside a torque coil, mechanical torque cannot be uniformly transmitted from the proximal part to the scanning tip of the probe. The problem becomes even worse when a rotational scanning is performed in conditions under which the endoscopic probe is inserted into a narrow path with a high curvature. Since the optical fiber and the signal wire are not configured with rotational symmetry around the central axis of the torque coil in existing PAE probes, mechanical torque cannot be uniformly transmitted from the proximal part to the scanning tip of an endoscopic probe when the probe is bent with a high curvature, thereby decreasing the quality of the image.

When the proximal part of the torque coil rotates by a specific angle but the scanning tip at the opposite end fails to rotate by the same angle, and when the difference varies greatly with various probe curvature, the reliability of the obtained image is seriously reduced and it is also impossible to produce a reliable 3D image based on the acquired series of 2D cross-sectional images. Accordingly, in the related art, avoiding the non-uniform rotational motion of the scanning tip is regarded as a very important issue, with the use of the technical term "non-uniform rotational distortion (NURD)". However, no prior PAE systems have satisfactorily solved the two aforementioned technical problems, i.e., the flexibility of the entire probe section and the rotational uniformity of the scanning tip.

In addition to the major problems described above, since the endoscopic system disclosed in Prior Document 4 using a torque coil-based proximal actuation mechanism and other PAE systems that are similar do not include such system element as a plastic catheter or sheath as a protective cover for the entire endoscopic probe, which is commonly equipped in EUS mini-probes utilized for the diagnosis of digestive diseases and IVUS catheter probes utilized for the diagnosis of cardiovascular diseases, no specific structures or methods also have been provided for isolating the scanning tip from an object to be examined and thus protecting the object when the scanning tip of the probe physically rotates. In addition to the previously mentioned basic functions, covering the entire scanning tip and the torque coil with a plastic catheter has another important technical aspect. Like existing EUS mini-probes developed to be inserted into the instrument channel of a video endoscope, in a PAE probe developed to be used in a similar manner, an appropriate acoustic matching liquid medium has to be filled inside the probe, and the probe has to be permanently sealed. However, prior PAE systems (in Prior Documents 4 and 8) fail to provide a specific structure or method for covering the entire scanning tip and the torque coil with a plastic catheter.

In other words, in a PAE system using a torque coil-based proximal actuation mechanism, a method of appropriately sealing the entire scanning tip and the entire torque coil section that physically rotate inside a plastic catheter and effectively implementing a rotary optical and electromagnetic coupler at the proximal part of the probe is very important. However, the method is not specifically disclosed in the prior documents.

Additional aspects will be set forth in part in the description which follows and, in part, will be apparent from the description, or may be learned by practice of the presented embodiments.

According to one or more embodiments, a photoacoustic-ultrasonic (i.e. dual-mode) endoscope includes a probe and a probe driving unit, wherein the probe includes: a coaxially configured optical and electromagnetic rotary waveguide assembly including an optical fiber and a conductive path, wherein the optical fiber includes a core and a cladding, and the conductive path is coaxially arranged with the optical fiber; a scanning tip located at an end of the coaxially configured optical and electromagnetic rotary waveguide assembly and configured to deliver a laser beam to an object to be examined and detect a photoacoustic signal and an ultrasonic signal generated from the object to be examined; and a plastic catheter surrounding outer surfaces of the coaxially configured optical and electromagnetic rotary waveguide assembly and the scanning tip, wherein the conductive path includes: a first conductive path including a portion coaxially arranged with the optical fiber; and a second conductive path including a portion coaxially arranged with the optical fiber and insulated from the first conductive path.

The first conductive path may surround the optical fiber, and the second conductive path may be coaxially arranged with the first conductive path and surround the first conductive path.

At least one from among the first conductive path and the second conductive path may have a tubular shape.

At least one from among the first conductive path and the second conductive path may include a torque coil set formed as a coil outside the optical fiber.

Each of the first conductive path and the second conductive path may surround at east a portion of the optical fiber.

The coaxially configured optical and electromagnetic rotary waveguide assembly may include an insulating coating layer between the first conductive path and the second conductive path.

The cladding may include a first cladding configured to propagate light waves and a second cladding surrounding the first cladding.

According to one or more embodiments, a photoacoustic-ultrasonic (i.e. dual-mode) endoscope includes a probe and a probe driving unit, wherein the probe includes: a coaxially configured optical and electromagnetic rotary waveguide assembly including an optical fiber and a conductive path, wherein the optical fiber includes a core and a cladding, and the conductive path is coaxially arranged with the optical fiber; a scanning tip located at an end of the coaxially configured optical and electromagnetic rotary waveguide assembly and configured to deliver a laser beam to an object to be examined and detect a photoacoustic signal and an ultrasonic signal generated from the object to be examined; a plastic catheter surrounding outer surfaces of the coaxially configured optical and electromagnetic rotary waveguide assembly and the scanning tip; and a rotary transformer electrically connected to the conductive path, and the probe driving unit includes: an optical inputter configured to deliver light energy to the optical fiber, wherein the optical fiber rotates; and an ultrasonic pulser-receiver electrically connected to the rotary transformer.

The rotary transformer may include: a primary coil unit electrically connected to the conductive path; and a secondary coil unit facing the primary coil unit and electrically connected to the ultrasonic pulser-receiver.

The photoacoustic-ultrasonic (i.e. dual-mode) endoscope may further include a mesh reinforcement inside the plastic catheter.

The probe may further include an injection port.

The photoacoustic-ultrasonic (i.e. dual-mode) endoscope may further include: a guiding catheter surrounding the plastic catheter and including a guiding catheter injection port; and a guiding wire inserted into the guiding catheter injection port.

The photoacoustic-ultrasonic endoscope may further include a light source for optical coherence tomography (OCT), wherein the light source is configured to supply light waves for OCT to the optical fiber.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
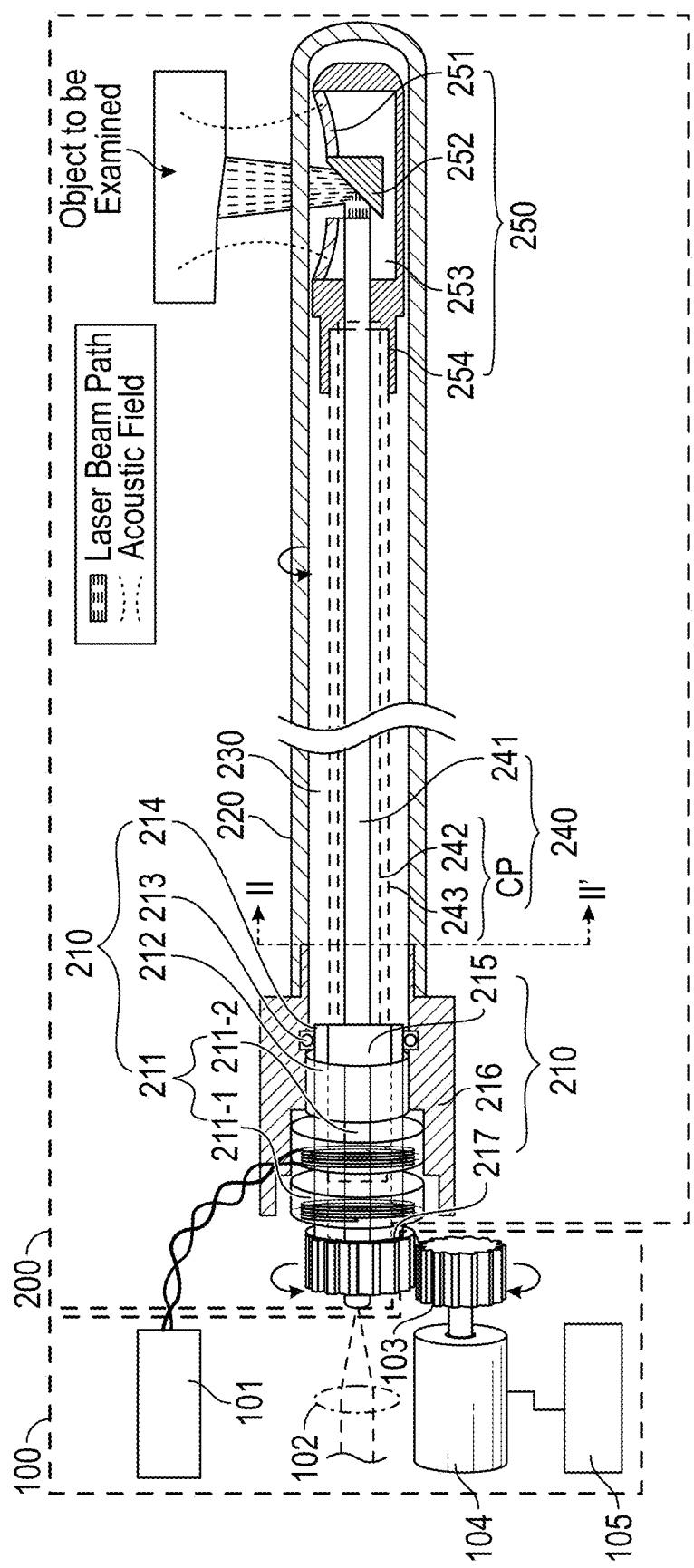
FIG. 1 is a view illustrating a configuration of a photoacoustic-ultrasonic endoscope including a coaxially configured optical and electromagnetic rotary waveguide assembly and a rotary optical and electromagnetic coupler, according to an embodiment.

The present disclosure may include various embodiments and modifications, and embodiments thereof will be illustrated in the drawings and will be described herein in detail. The advantages and features of the present disclosure and methods of achieving the advantages and features will be described more fully with reference to the accompanying drawings, in which embodiments are shown. The present disclosure may, however, be embodied in many different forms and should not be construed as being limited to the embodiments set forth herein.

Reference will now be made in detail to embodiments, examples of which are illustrated in the accompanying drawings. In the drawings, the same elements are denoted by the same reference numerals, and a repeated explanation thereof will not be given.

It will be understood that although the terms "first", "second", etc. may be used herein to describe various elements, these elements should not be limited by these terms. These elements are only used to distinguish one element from another.

As used herein, the singular forms "a", "an", and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when an element is referred to as being "connected to" another element, it may be directly or indirectly connected to the other element. That is, for example, intervening elements may be present.

As used herein, the term "and/or" includes any and all combinations of one or more of the associated listed items. Expressions such as "at least one of," when preceding a list of elements, modify the entire list of elements and do not modify the individual elements of the list.

FIG. 1 is a view illustrating a configuration of a photoacoustic-ultrasonic endoscope including a coaxially configured optical and electromagnetic rotary waveguide assembly and a rotary optical and electromagnetic coupler, according to an embodiment;

Referring to FIG. 1, the photoacoustic-ultrasonic endoscope (also referred to as a PAE-EUS system) according to an embodiment includes an imaging probe 200 (hereinafter, the imaging probe is referred to as a PAE-EUS probe) and a probe driving unit 100. The PAE-EUS probe 200 includes a coaxially configured optical and electromagnetic rotary waveguide assembly 240 including an optical fiber 241 including a core 241Co (see FIG. 7) and a cladding 241Cd (see FIG. 7), a conductive path CP coaxially arranged with the optical fiber 241, a scanning tip 250 located at one end (e.g., the distal end) of the coaxially configured optical and electromagnetic rotary waveguide assembly 240 and configured to deliver a laser beam to an object to be examined and detect a photoacoustic signal and an ultrasonic signal generated from the object to be examined, and a plastic catheter 220 surrounding outer surfaces of the coaxially configured optical and electromagnetic rotary waveguide assembly 240 and the scanning tip 250. The conductive path CP includes a first conductive path 242 including a portion coaxially arranged with the optical fiber 241 and a second conductive path 243 including a portion coaxially arranged with the optical fiber 241 and insulated from the first conductive path 242.

In order to solve the problems of the prior arts, the present disclosure provides the PAE-EUS probe 200 including the coaxially configured optical and electromagnetic rotary waveguide assembly (hereinafter, it is referred to as the waveguide assembly) 240, a rotary optical and electromagnetic coupler including an optical inputter 102, the optical fiber 241, a rotary transformer 211, and the probe driving unit 100 for driving the PAE-EUS probe 200.

The two concepts of the waveguide assembly 240 that includes the optical fiber 241, and the rotary optical and electromagnetic coupler that includes the optical inputter 102 and the rotary transformer 211, are respectively applied to a flexible section, i.e., the plastic catheter 220 section formed in the PAE-EUS probe 200 of FIG. 1 for insertion into the object to be examined and having a long and slender shape; and a base portion connected to the probe driving unit 100 at a proximal part 210 of the PAE-EUS probe 200.

Referring to FIG. 1, the PAE-EUS probe 200 is divided into a portion surrounded by the plastic catheter 220 and a portion that is the proximal part 210 physically surrounded by a base frame 216. Since the section surrounded by the plastic catheter 220 is physically flexible and has a long and slender tubular shape, the section may be effectively inserted into the object to be examined that may be accessible only through a narrow and curved path.

Also, since the plastic catheter 220 encloses the waveguide assembly 240 and the scanning tip 250 located in an inner space of the plastic catheter 220, and isolates the waveguide assembly 240 and the scanning tip 250 from an external space, the plastic catheter 220 prevents the waveguide assembly 240 and the scanning tip 250 from directly contacting the object to be examined. Also, the plastic catheter 220 may trap a matching liquid medium 230 filled in the plastic catheter 220 and may prevent the matching liquid medium 230 from leaking out. Since a laser beam and acoustic waves have to pass through a wall of the plastic catheter 220, the plastic catheter 220 may be formed of an optically transparent polymer-based material through which both the laser beam and acoustic waves may easily pass.

Although ultrapure water, such as deionized water, may be used as the matching liquid medium 230 filled in the inner space of the plastic catheter 220, it is preferable that a material used as the matching liquid medium 230 may be bio-friendly and may be usable semi-permanently, such as silicone oil (polydimethylsiloxane: PDMS) with a low viscosity and a high optical clarity. When water is used for the matching liquid medium 230, it is important to surely electrically insulate two conductive paths (which will be explained below) of the waveguide assembly 240 immersed in the matching liquid medium 230.

Since the plastic catheter 220 has a long and slender tubular shape, the plastic catheter 220 may be effectively inserted into the object to be examined that may be accessible only through a narrow and curved path. Accordingly, the plastic catheter 220 may be formed to have a diameter equal to or greater than about 1 mm and equal to or less than about 3 mm, and a total length equal to or greater than about 0.5 m and equal to or less than about 3 m.

The waveguide assembly 240 is located in the inner space of the plastic catheter 220 and extends from the proximal part 210 to the scanning tip 250. The waveguide assembly 240 is also physically flexible and delivers a photoacoustic signal and an ultrasonic signal detected by a piezoelectric element 251.

The scanning tip 250 is located at one end of the waveguide assembly 240. The scanning tip 250 delivers a laser beam guided through the optical fiber 241 in the waveguide assembly 240 or an ultrasonic pulse generated by the piezoelectric element 251 to the object to be examined, and also detects a photoacoustic signal generated in the object to be examined or an ultrasonic signal reflected from the object to be examined. The scanning tip 250 may include an optical reflector 252 that reflects a laser beam guided through the optical fiber 241 in the waveguide assembly 240 to a target point, the piezoelectric element 251 that generates a very short ultrasonic pulse or detects an ultrasonic signal or a photoacoustic signal generated from the object to be examined, a sound-absorbing backing layer 253 that may remove noise generated due to irregular reflection of sound waves, and a metal casing 254 that surrounds the piezoelectric element 251, the optical reflector 252, and the sound-absorbing backing layer 253.

The proximal part 210 that is connected to the waveguide assembly 240 and receives mechanical torque from the probe driving unit 100 and transmits the mechanical torque to the waveguide assembly 240 is located at the other end of the waveguide assembly 240. The proximal part 210 may include a proximal gear 217, the rotary transformer 211, a ball bearing module 212, a sealing O-ring 213, a hollowed shaft 214, an epoxy filler 215, and the base frame 216 that surrounds the rotary transformer 211, the ball bearing module 212, the sealing O-ring 213, the hollowed shaft 214, the epoxy filler 215, and the proximal gear 217.

The proximal gear 217 receives mechanical torque from the probe driving unit 100 and transmits the mechanical torque to the waveguide assembly 240. The rotary transformer 211 is located in the proximal part 210 and receives an electrical pulse generated from an ultrasonic puller-receiver 101 and transmits the electrical pulse to the piezoelectric element 251 or receives an electrical signal generated from the piezoelectric element 251 and transmits the electrical signal to the ultrasonic pulser-receiver 101. Any electrical signal in the two processes passes through the waveguide assembly 240.

The sealing O-ring 213 prevents the matching liquid medium 230 filled inside the plastic catheter 220 from leaking out. The ball bearing module 212 provides a mechanical condition in which the hollowed shaft 214 may smoothly rotate at a stable position.

The probe driving unit 100 is a physically independent unit that may be separated from the PAE-EUS probe 200. The probe driving unit 100 may include the ultrasonic pulser-receiver 101 that may transmit or receive an electrical signal to or from the rotary transformer 211 and may amplify a received electrical signal; the optical inputter 102 that inputs a laser pulse to the optical fiber 241 that rotates, by constituting a rotary optical coupler along with the optical fiber 241; a driving gear 103 that transmits mechanical torque to the waveguide assembly 240; an actuator 104 coupled to the driving gear 103; and an actuator driver 105 that controls the actuator 104, which will be explained below.

The elements illustrated in FIG. 1 are just essential elements needed to explain the major result derived from the present disclosure, and system elements that are obviously required according to common sense may be added if necessary. For example, the metal casing 254 may be formed with multiple pieces rather than a single piece of metal.

The optical fiber 241 and the conductive path CP included in the waveguide assembly 240 will now be explained.

Figure 2:
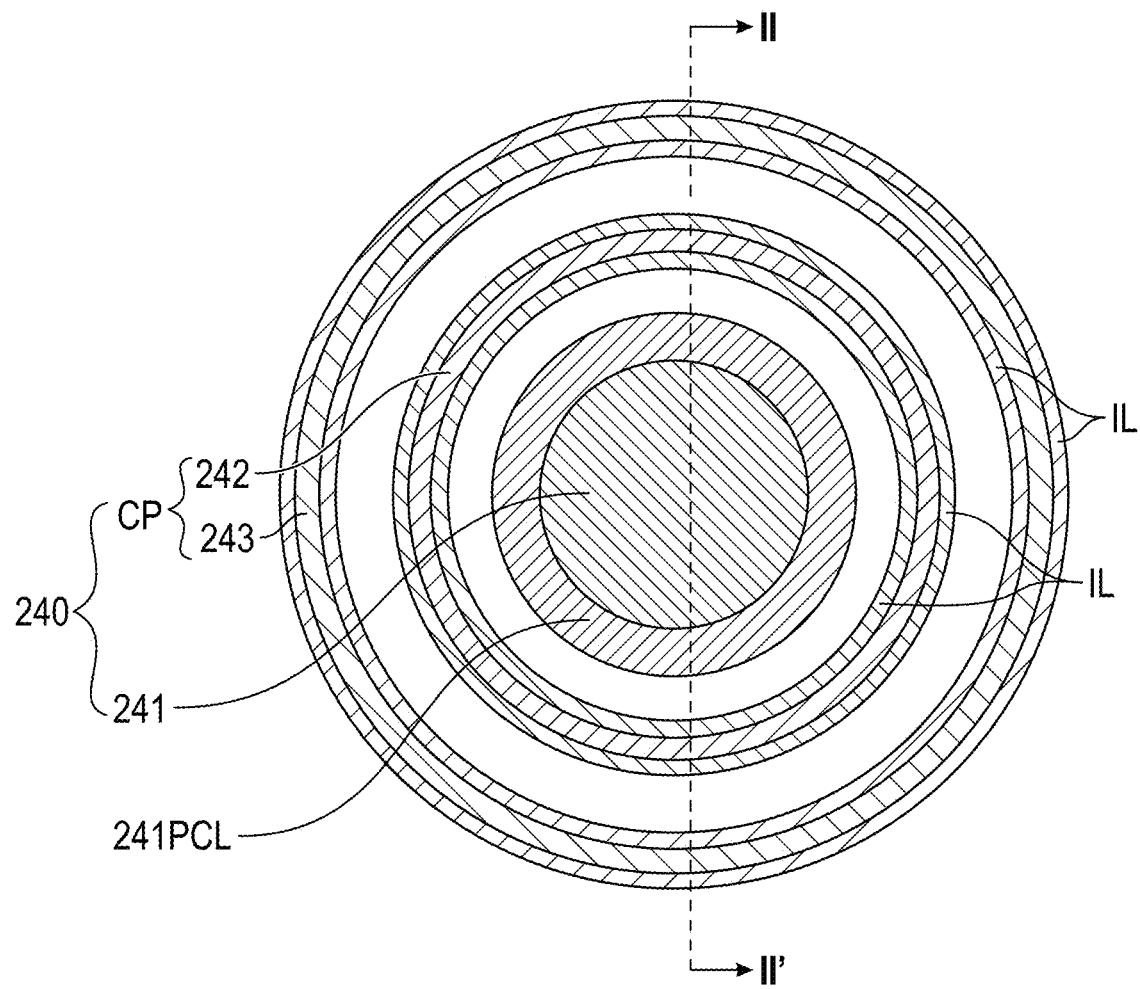
FIG. 2 is a cross-sectional view taken along line II-II' of FIG. 1.

FIG. 2 is a cross-sectional view taken along line of FIG. 1.

Referring to FIG. 2, the optical fiber 241 generally includes a core and a cladding, and may include a protective coating layer 241PCL formed of a polymer or the like outside the core and the cladding. The conductive path CP that is coaxially arranged with the optical fiber 241, surrounds the optical fiber 241, and delivers an electrical signal, is located outside the optical fiber 241. The conductive path CP includes the first conductive path 242 including a portion coaxially arranged with the optical fiber 241, and the second conductive path 243 including a portion coaxially arranged with the optical fiber 241 and insulated from the first conductive path 242.

The key feature of the present disclosure is that the optical fiber 241, the first conductive path 242, and the second conductive path 243 are all coaxially arranged along one reference point, i.e., the central axis of the waveguide assembly 240, and rotate together as an integrative unit at the same angular speed during the rotation, which will be explained below.

According to an embodiment, a first conductive path 242 may surround the optical fiber 241, and a second conductive path 243 may be coaxially arranged with the first conductive path 242 and may surround the first conductive path 242. That is, cross-sections of the optical fiber 241, the first conductive path 242, and the second conductive path 243 may have concentric circular shapes as shown in FIG. 2. In this case, at least one of the first conductive path 242 and the second conductive path 243 may have a tubular shape. When at least one of the first conductive path 242 and the second conductive path 243 has a tubular shape, the first conductive path 242 and/or the second conductive path 243 has a hollowed tubular shape with a predetermined thickness and surrounds an outer surface of the optical fiber 241. In this case, at least one of the first conductive path 242 and the second conductive path 243 may be formed by directly coating a conductive material on the outer surface of the optical fiber 241 by using, for example, sputtering or vapor deposition.

In order to insulate the first and second conductive paths 242 and 243, a surface of each of the first and second conductive paths 242 and 243 may be coated with an insulating layer IL. The insulating layer IL may include a polymer. Alternatively, a tubular structure made of an insulating material may be additionally inserted between the first and second conductive paths 242 and 243.

Referring back to FIGS. 1 and 2, the optical fiber 241 is located at the center of the waveguide assembly 240, and the first conductive path 242 and the second conductive path 243 are coaxially arranged outside the optical fiber 241. In this particular structure, the optical fiber 241 located at the center functions as an optical waveguide that delivers laser light, and the first and second conductive paths 242 and 243 function as an electromagnetic waveguide that may deliver a high frequency electrical signal (typically in a radio frequency (RF) range) very effectively, like the electric coaxial cables that are commonly utilized in many RF devices. For reference, the typical frequency of an electrical signal used herein may range from about 0.1 MHz to about 100 MHz, and the optical fiber 241 used herein may be a multi-mode optical fiber, a single-mode optical fiber, or a combination thereof, according to a desired purpose of an application.

In addition to functioning as an optical and electromagnetic waveguide, the waveguide assembly 240 may also function as a flexible shaft that transmits mechanical torque from the proximal part 210 to the scanning tip 250, when the optical fiber 241, the first conductive path 242, and the second conductive path 243 are effectively formed as an integrated single unit of mechanical components, which is another important feature different from the prior arts. Accordingly, the first conductive path 242 and the second conductive path 243 have to have shapes or structures that may be easily bent. If there is a physical interval or gap between the optical fiber 241 and the first and second conductive paths 242 and 243, for example, the waveguide assembly 240 may be more flexibly bent and effectively transmit mechanical torque.

In short, the present disclosure is characterized by the unique system feature that a waveguide assembly 240 capable of transmitting not only laser light and an electrical signal but also a very uniform mechanical torque based on the rotationally symmetric structure is employed in a PAI-EUS system that operates based on a single-element ultrasonic transducer-based proximal actuation mechanism.

Figure 3:
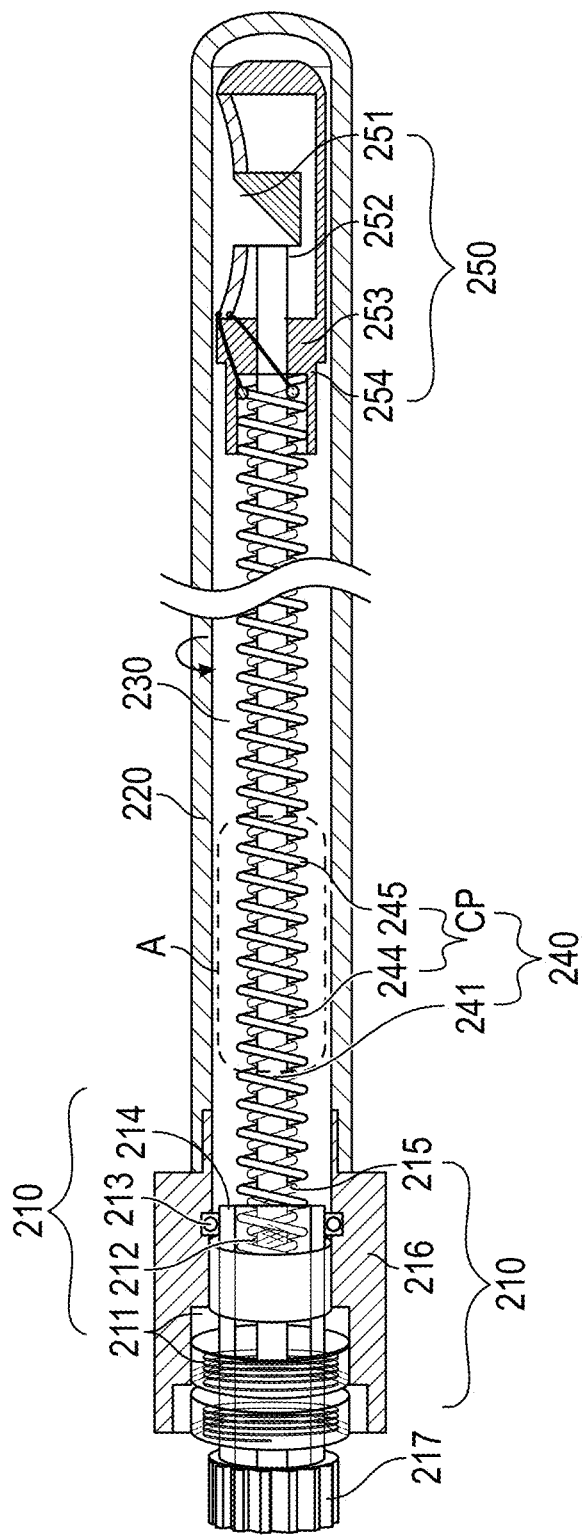
FIG. 3 is a view illustrating a configuration of a coaxially configured optical and electromagnetic rotary waveguide assembly in a photoacoustic-ultrasonic endoscope, according to another embodiment.
Figure 4:
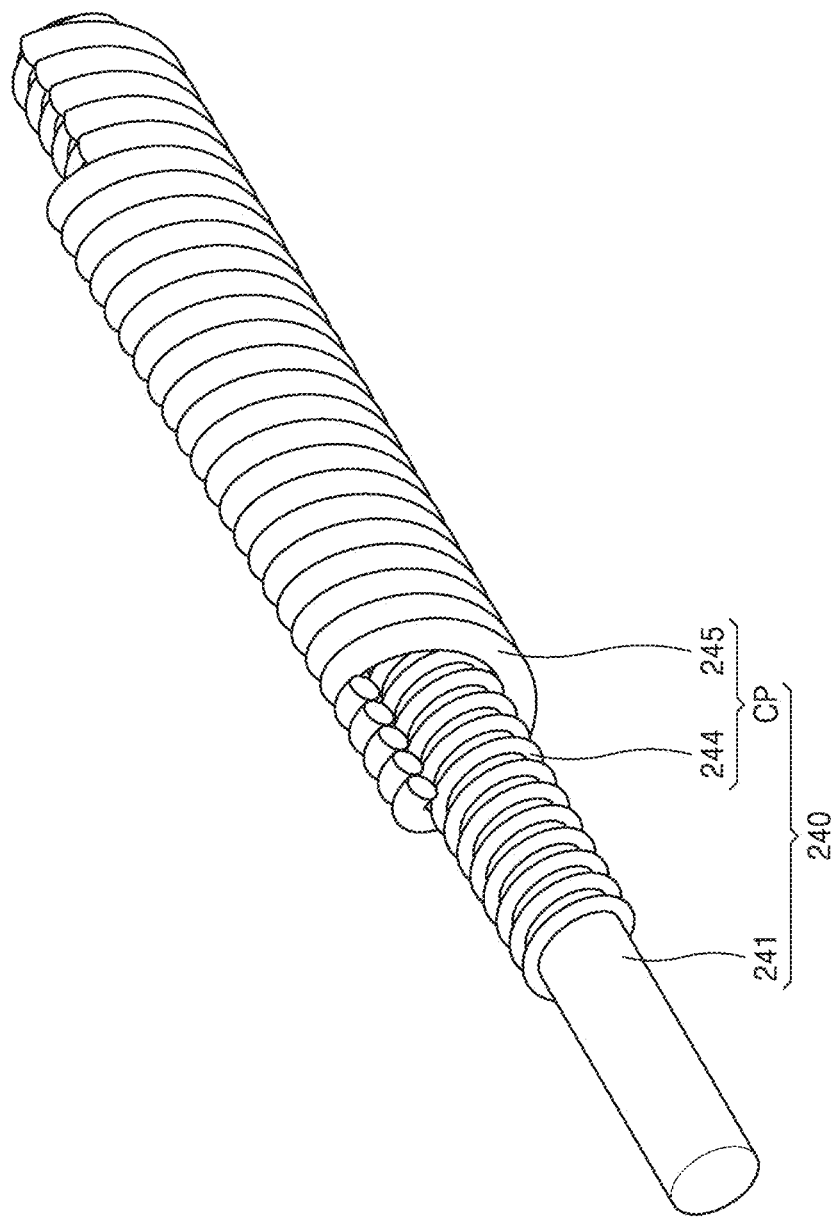
FIG. 4 is a perspective view illustrating a detailed configuration of a portion A of the coaxially configured optical and electromagnetic rotary waveguide assembly of FIG. 3.
Figure 5:
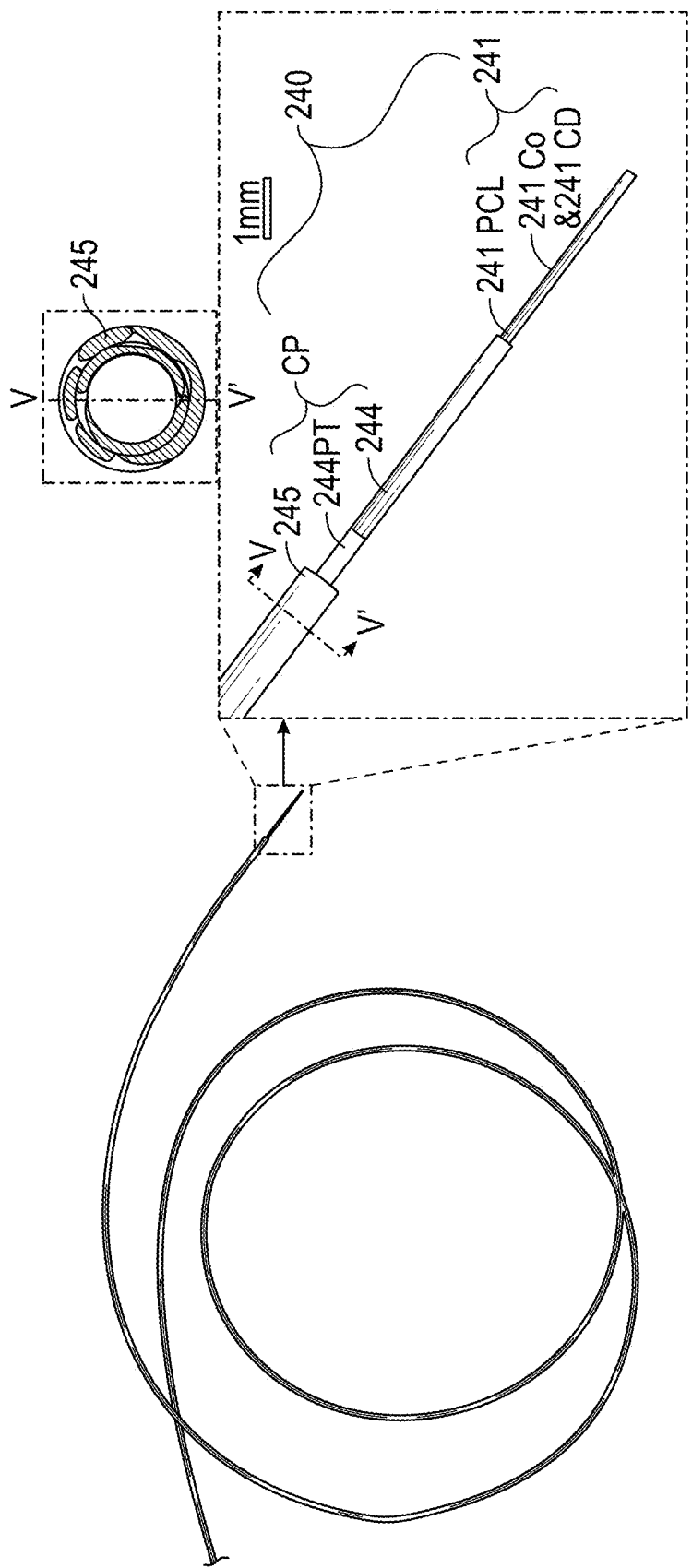
FIG. 5 is a photo showing a real embodiment of the coaxially configured optical and electromagnetic rotary waveguide assembly according to the structure shown in FIG. 4.

FIG. 3 is a view illustrating a configuration of a coaxially configured optical and electromagnetic rotary waveguide assembly in a photoacoustic-ultrasonic endoscope, according to another embodiment. FIG. 4 is a perspective view illustrating a detailed configuration of a portion A of FIG. 3. FIG. 5 is a photo showing a real embodiment of the waveguide assembly 240 according to the structure shown in FIG. 4. In particular, FIG. 3 illustrates how the waveguide assembly 240 according to this specific embodiment is installed and electrically connected in the PAE-EUS probe 200.

As described above, the waveguide assembly 240 includes the optical fiber 241 that may deliver light, and the conductive path CP including a first conductive path including a portion coaxially arranged with the optical fiber 241 and a second conductive path including a portion coaxially arranged with the optical fiber 241 and insulated from the first conductive path 242.

According to an embodiment, the first conductive path 244 may surround the optical fiber 241, the second conductive path 245 may be coaxially arranged with the first conductive path 244 and may surround the first conductive path 244, and at least one of the first conductive path 244 and the second conductive path 245 may include a torque coil set formed as a coil and located outside the optical fiber 241.

Referring to FIG. 4, the first conductive path 244 and the second conductive path 245, which surround the optical fiber 241, may include torque coil sets 244 and 245. Here, the torque coil sets 244 and 245 are respectively referred to as an inner torque coil set 244 and an outer torque coil set 245. The reason that the term "set" is attached to each name is because each torque coil may have a single-layered structure as shown in FIG. 4 or a multi-layered structure in which multi-layered torque coils overlap and function as one unit. For example, referring to FIG. 5, each torque coil set 244 or 245 may have a two-layered structure composed of a plurality of wires (see the cross-sectional view). This structure may, in general, more effectively transmit mechanical torque over a very long probe section greater than 1 m. When a given space is limited and the flexibility of a probe is relatively more important, each torque coil set 244 or 245 may have a single-layered structure as shown in FIG. 4.

In order to increase the electrical conductivity of each of the inner and outer torque coil sets 244 and 245, the surface of each of the inner and outer torque coil sets 244 and 245 may be coated or plated with a material that has high electrical conductivity, if necessary. Alternatively, the entire bodies of the torque coil sets 244 and 245 may be fabricated with a single material that has high electrical conductivity. In either case, in order to electrically insulate the inner and outer torque coil sets 244 and 245, the outermost surface of each of the inner and outer torque coil sets 244 and 245 may be coated with a polymer-based insulating material, or a thin-wall tube 244PT (see FIG. 5) formed of a polymer may be inserted between the inner and outer torque coil sets 244 and 245. Any of these two methods may be used in an embodiment.

Although a method of implementing the waveguide assembly 240 by using torque coil sets has been described with reference to FIG. 5, the waveguide assembly 240 may be implemented by applying a method of inserting and overlapping two conductive tubes each having a small wall thickness, instead of using torque coils.

Referring back to FIG. 3, the inner torque coil set 244 functioning as a first conductive path and the outer torque coil set 245 functioning as a second conductive path are respectively connected to the two electrodes of the piezo-electric element 251 and provide a path through which an electric current flows from the scanning tip 250 to the rotary transformer 211 located in the proximal part 210. The inner and outer torque coil sets 244 and 245 included in the waveguide assembly 245 are also electrically connected to a primary coil unit 211-1, which is a left coil unit, of the rotary transformer 211 that rotates along with the inner and outer torque coil sets 244 and 245.

Figure 6:
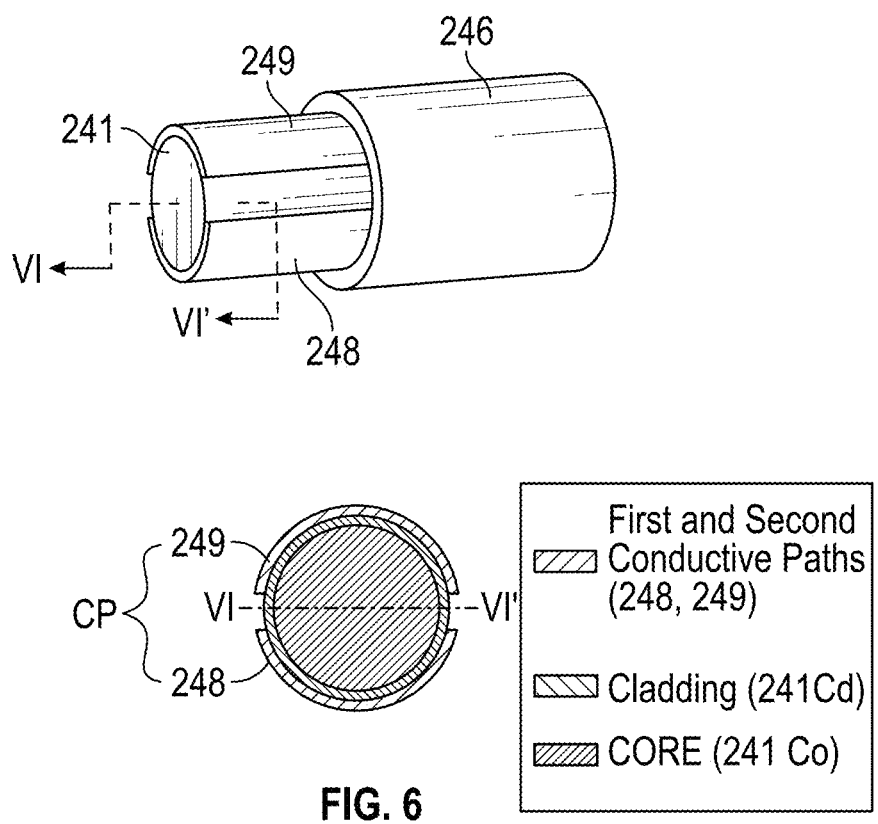
FIG. 6 shows a perspective view and a cross-sectional view illustrating a configuration of the coaxially configured optical and electromagnetic rotary waveguide assembly according to an embodiment.
Figure 7:
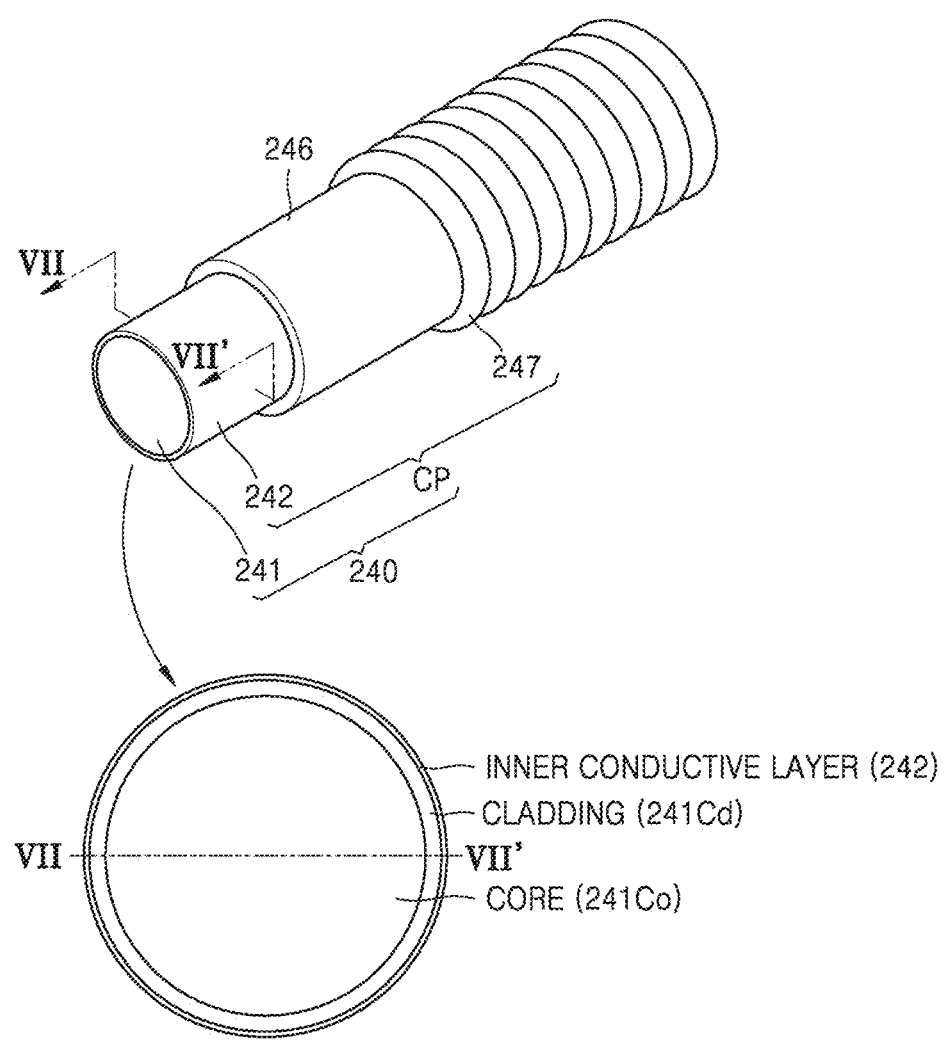
FIG. 7 shows a perspective view and a cross-sectional view illustrating a configuration of the coaxially configured optical and electromagnetic rotary waveguide assembly according to another embodiment.

FIGS. 6 and 7 show a perspective view and a cross-sectional view illustrating a configuration of the coaxially configured optical and electromagnetic rotary waveguide assembly according to respective embodiments.

Referring to an embodiment of FIG. 6, a first conductive path 248 and a second conductive path 249 may surround at least a portion of the optical fiber 241. Referring to a cross-sectional view of the waveguide assembly 240 of FIG. 6 taken along line VI-VI', the conductive path CP is divided into the first conductive path 248 having a U shape and the second conductive path 249 having an inverted-U shape. Each of the first and second conductive paths 248 and 249 surrounds a part of the optical fiber 241. In this case, since the first conductive path 248 and the second conductive path 249 of the conductive path CP are geometrically coaxial with the optical fiber 241 and provide a path through which an electric current flows, even when the waveguide assembly 240 is bent, the conductive path CP may transmit mechanical torque very uniformly. An insulating coating layer 246 that prevents electricity leakage due to contact with the matching liquid medium 230 may be formed on an outer surface of the conductive path CP.

Referring to FIG. 7, the waveguide assembly 240 according to an embodiment may include the insulating coating layer 246 located between the first conductive path 242 (that is, an inner conductive layer) and a second conductive path 247. That is, the waveguide assembly 240 may be configured so that the first conductive path 242 surrounding the entire surface of the cladding 241Cd of the optical fiber 241 and having a tubular shape, the insulating coating layer 246 surrounding the entire outer surface of the first conductive path 242, and the second conductive path 247 embodied with a torque coil set are sequentially located from inside to outside in this stated order. In this case, the insulating coating layer 246 electrically insulates the first and second conductive paths 242 and 247. In this embodiment, the first conductive path 242 may be directly coated on the entire surface of the cladding 241Cd of the optical fiber 241.

A structure of FIGS. 6 and 7 may be more effectively applied to an intravascular imaging endoscope in which an overall diameter of a probe has to be very small.

Figure 8:
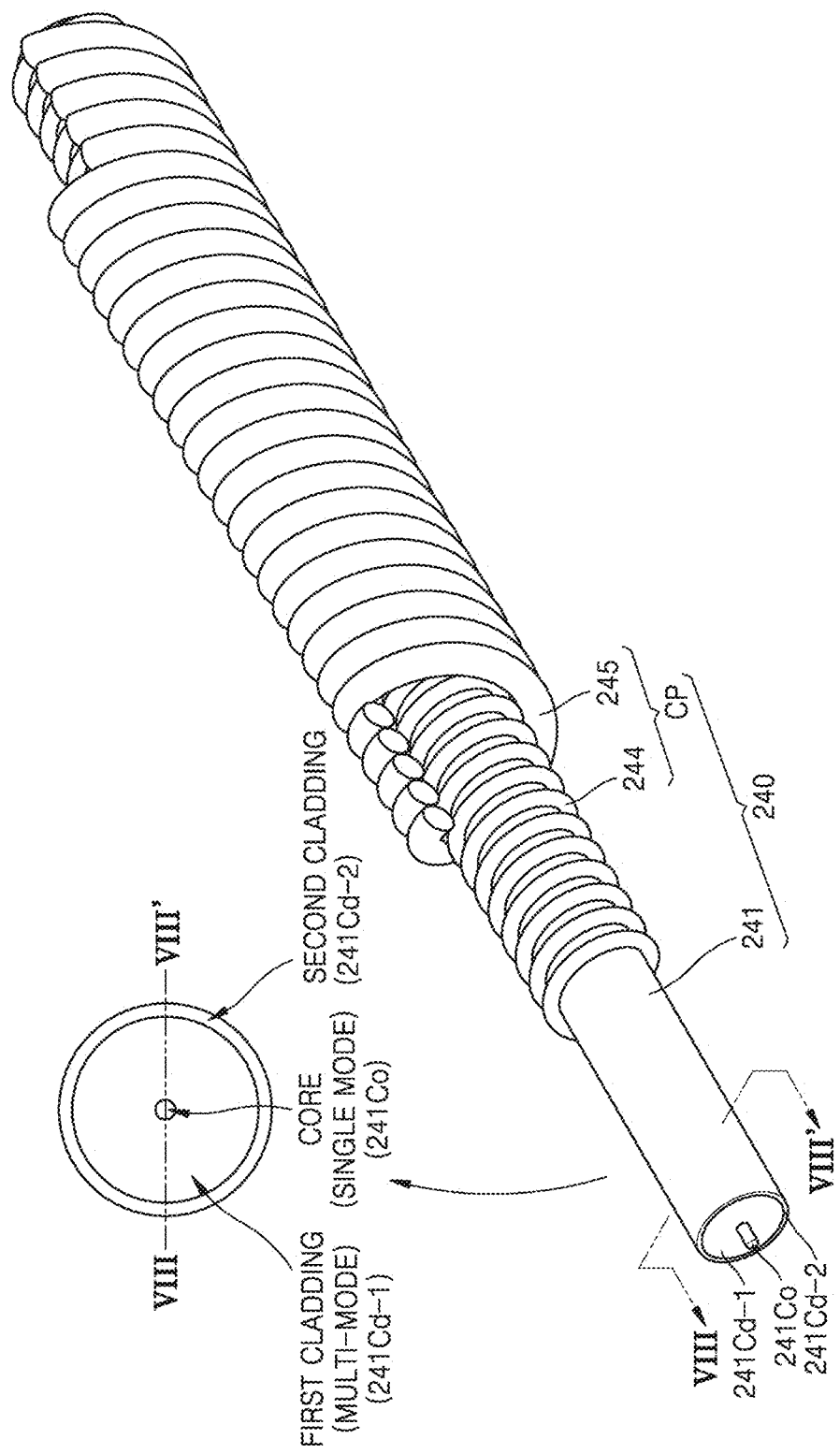
FIG. 8 shows a perspective view and a cross-sectional view of the coaxially configured optical and electromagnetic rotary waveguide assembly including a double-clad optical fiber according to an embodiment.

FIG. 8 shows a perspective view and a cross-sectional view of the coaxially configured optical and electromagnetic rotary waveguide assembly including a double-clad optical fiber, according to an embodiment.

According to this embodiment, the optical fiber 241 of the waveguide assembly 240 may include not only the core 241Co and a first cladding 241Cd-1 that surrounds the core 241Co and may deliver light but also a second cladding 241Cd-2 that surrounds the first cladding 241Cd-1.

In FIG. 1, the waveguide assembly 240 selectively uses a multi-mode optical fiber or a single-mode optical fiber. In general, the multi-mode optical fiber has advantages in that the multi-mode optical fiber may transmit a large amount of light energy. On the other hand, although the total energy delivered by the single-mode optical fiber is small, the single-mode optical fiber has advantages in that the single-mode optical fiber may be able to more easily focus laser light in conjunction with a lens or the like mounted at the distal end of the optical fiber. When a large amount of light energy needs to be delivered and the light needs to be focused as well, the waveguide assembly 240 may include the optical fiber 241 with a double cladding structure as shown in FIG. 8. In the optical fiber 241 with a double cladding structure, as shown in a cross-sectional view of the waveguide assembly 240 of FIG. 8 taken along line the core 241Co that may deliver single-mode optical waves is located at the center and the first cladding 241Cd-1 that may deliver multi-mode optical waves is located outside the core 241Co and surrounds the core 241Co. In this case, the second cladding 241Cd-2 is located at the outermost position so that the first cladding 241Cd-1 functions as an optical fiber that may also propagate light.

When the optical fiber 241 and the first and second conductive paths 244 and 245 of the conductive path CP are coaxially arranged as described above, the mechanical torque applied to the proximal part 210 may be uniformly transmitted to the scanning tip 250 located at an end of the PAE-EUS probe 200.

Referring back to FIG. 1, The PAE-EUS system including the rotary transformer 211 and the rotary optical coupler including the optical inputter 102 and the optical fiber 241 will now be explained. For reference, the rotary transformer 211 and the rotary optical coupler including the optical inputter 102 and the optical fiber 241 are collectively referred to as a rotary optical and electromagnetic coupler, i.e., a unit including the rotary transformer 211, the optical inputter 102, and the optical fiber 241.

The PAE-EUS system according to an embodiment includes the PAE-EUS probe 200 and the probe driving unit 100. The PAE-EUS probe 200 includes the waveguide assembly 240 including the optical fiber 241, including the core 241Co (see FIG. 7) and the cladding 241Cd (see FIG. 7), and the conductive path CP, coaxially arranged with the optical fiber 241, the scanning tip 250 located at an end of the waveguide assembly 240 and configured to deliver a laser beam to the object to be examined and detect a photoacoustic signal and an ultrasonic signal generated from the object to be examined, the plastic catheter 220 surrounding outer surfaces of the waveguide assembly 240 and the scanning tip 250, and the rotary transformer 211 electrically connected to the conductive path CP. The probe driving unit 100 includes the optical inputter 102 that delivers light energy to the optical fiber 241 which rotates and the ultrasonic puller-receiver 101 that is electrically connected to the rotary transformer 211.

The rotary transformer 211 refers to an electric element in which the primary coil unit 211-1 in which an electric wire wound along an inner or side edge of a magnetic core with a ring shape to be parallel to the magnetic core forms one group, and the secondary coil unit 211-2 in which another electric wire with the same structure as that of the electric wire of the primary coil unit 211-1 forms another group, the two groups facing each other so as to be symmetric with each other.

The primary coil unit 211-1 is electrically connected to the conductive path CP of the waveguide assembly 240 and the secondary coil unit 211-2 is electrically connected to an output/input port (not shown) of the ultrasonic pulser-receiver 101. Accordingly, when the proximal gear 217 starts to rotate and thus even the waveguide assembly 240, the hollowed shaft 214 connected to the waveguide assembly 240, and the primary coil unit 211-1 with a ring shape formed around the hollowed shaft 214 also rotate together, the base frame 216 and the secondary coil unit 211-2 do not rotate due to the ball bearing module 212. That is, unlike the primary coil unit 211-1 electrically connected to the first and second conductive paths 242 and 243 of the waveguide assembly 240, the secondary coil unit 211-2 is fixed to the base frame 216 and does not rotate. As a result, an electrical signal may be input/output to/from the rotating waveguide assembly 240 without the problem in which any pair of electric wires are intertwined.

That is, the rotary transformer 211 is a key electrical element that operates based on the electromagnetic induction principle and may transmit/receive an electrical signal without any direct physical contact between two relatively moving objects or through wires. Although the rotary transformer 211 has limitations in that the rotary transformer 211 may deliver only an alternating current (AC) signal due to the electromagnetic induction principle, the rotary transformer 211 has key advantages in that the rotary transformer 211 may transmit/receive an electrical signal to/from a rotating body without direct physical contact with the rotating body. Also, by appropriately selecting the winding turns ratio between the electric wires of the two groups, the rotary transformer 211 may change a voltage or electrical impedance when delivering an electrical signal. Regarding the position of the rotary transformer 211, it may be switched with the ball bearing module 212 or the proximal gear 217.

The optical inputter 102 that is, for example, a convex lens or an objective lens, inputs laser light into the optical fiber 241 that rotates. That is, when a laser pulse is generated by a light source 300 (see FIG. 13), the laser pulse propagates through a separate guiding optical fiber (not shown) to the optical inputter 102. In this case, the optical inputter 102 delivers the guided laser pulse to the optical fiber 241 placed along the central axis of the waveguide assembly 240. The important feature is that the optical fiber 241 of the waveguide assembly 240 rotates whereas the optical inputter 102 delivers laser light in a static condition, i.e., without any physical rotation. That is, the optical inputter 102 that inputs laser light and the optical fiber 241 that receives the laser light constitute a virtually paired unit, called "rotary optical coupler".

If necessary, instead of the optical inputter 102, such as a convex lens or an objective lens, shown in FIG. 1, a rotary optical coupler may be formed to have an alternative configuration in which the guiding optical fiber (not shown) is directly engaged with the optical fiber 241 of the waveguide assembly 240. In this case, the end of the guiding optical fiber has to be positioned as close to the optical fiber 241 of the waveguide assembly 240 as possible. Also, it is preferable that optical fibers with the same specifications are used for the guiding optical fiber and the optical fiber 241 of the waveguide assembly 240 so that light energy may be more effectively delivered through the junction.

The ultrasonic puller-receiver 101 is electrically connected to the rotary transformer 211 and receives a photoacoustic signal and an ultrasonic signal detected or electrically converted by the piezoelectric element 251, which will be explained below.

Figure 9:
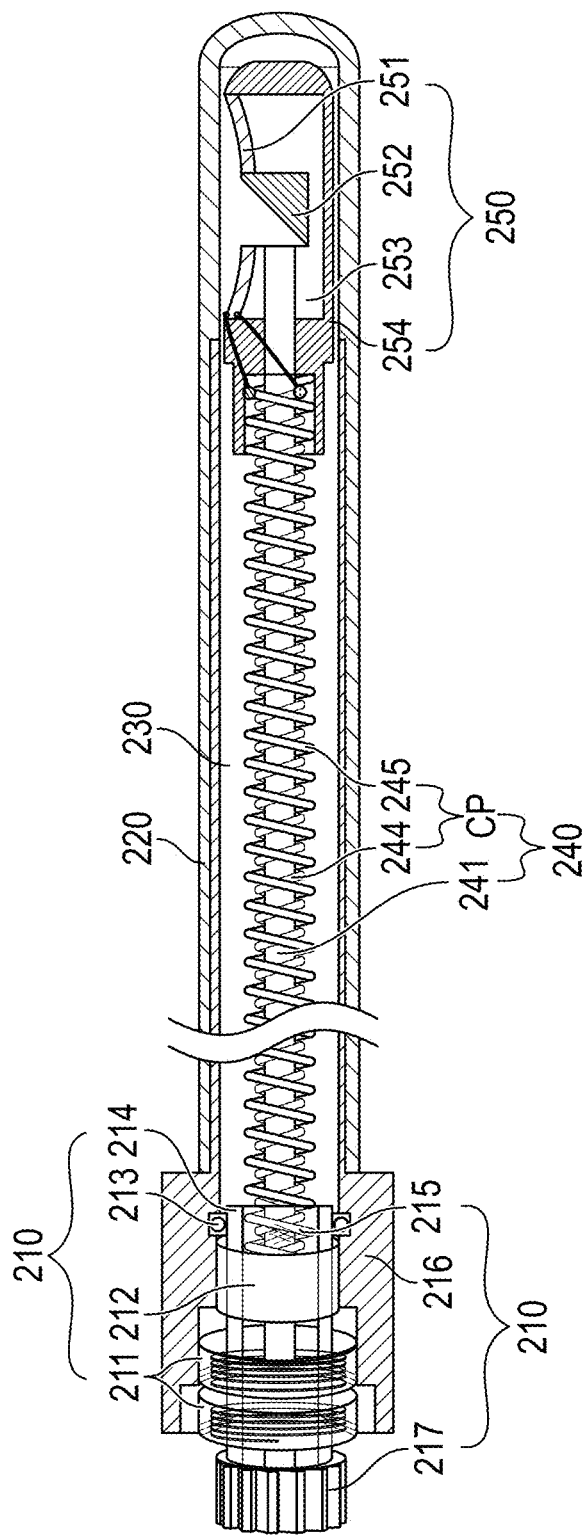
FIG. 9 is a view illustrating a structure and a configuration of a metal-mesh embedded plastic catheter, according to an embodiment.
Figure 10:
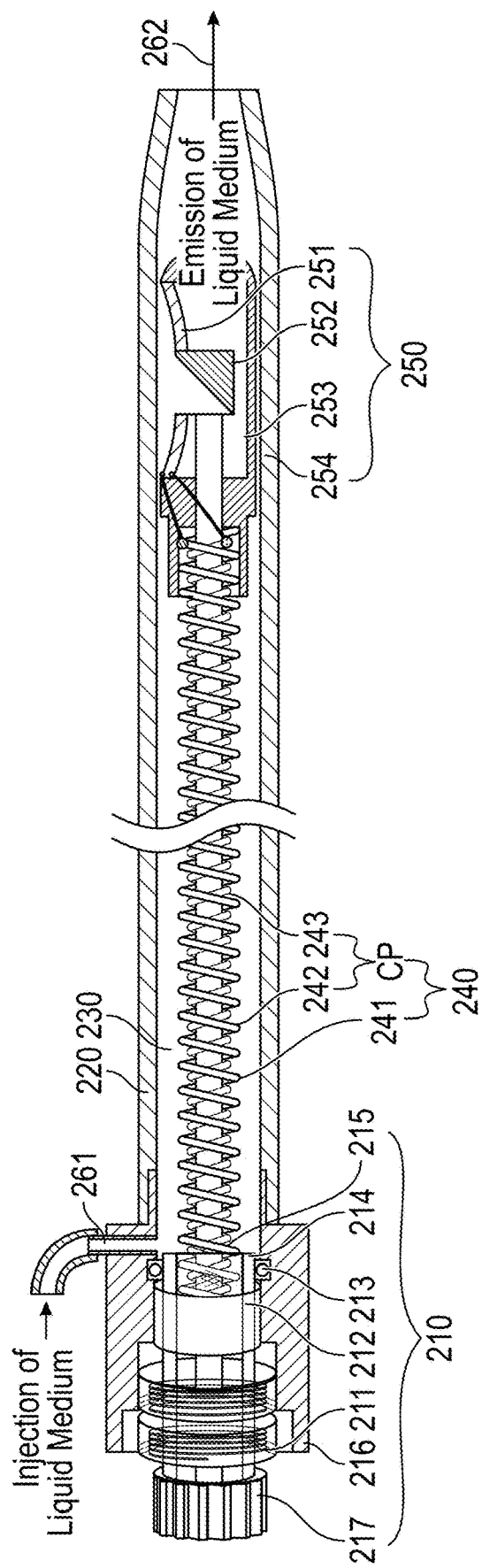
FIG. 10 is a view for explaining a shape and a structure of the plastic catheter modified to be used for intravascular endoscopy and a method of injecting a liquid medium, according to an embodiment.
Figure 11:
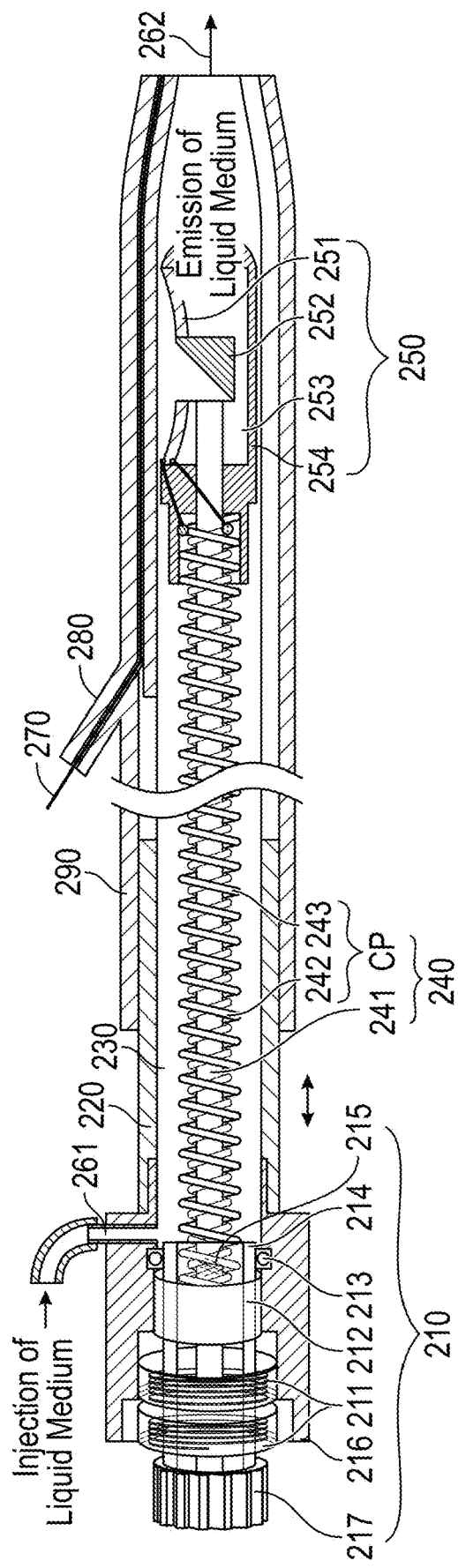
FIG. 11 is a view for explaining a configuration of the plastic catheter to be used with a guiding wire, and a process of performing a pullback scanning, according to an embodiment.

FIGS. 9 through 11 are views each illustrating a variation of the PA probe 200 from the basic configuration shown in FIG. 1, according to an embodiment.

FIG. 9 is a view illustrating a structure and a configuration of a metal-mesh embedded plastic catheter according to an embodiment.

According to an embodiment, the PAE-EUS system may further include a reinforcement 260 located inside the plastic catheter 220. Referring to FIG. 9, the reinforcement 260 is a braided or mesh reinforcement made of a metal material that may be embedded into the plastic catheter 220. Accordingly, a lifetime of the plastic catheter 220 may be extended.

FIG. 10 is a view for explaining a shape and a structure of the plastic catheter modified to be used for intravascular endoscopy, and a method of injecting a liquid medium, according to an embodiment.

Referring to an embodiment of FIG. 10, the base frame 216 may further include an injection port 261. When the PAE-EUS probe 200 of the present disclosure is to be used by a method in which the probe is not inserted into the instrument channel of a video endoscope currently used in clinics, an outlet port 262 may be formed by opening an end portion of the plastic catheter 220, the injection port 261 may be additionally provided in the base frame 216, and the PAE-EUS probe 200 may be used for the diagnosis of intravascular diseases, like an existing IVUS catheter probe. In this case, the liquid medium injected through the injection port 261 may be a saline solution; then, the matching liquid medium 230 filled in an inner space of the PAE-EUS probe 200 will be the same saline solution.

FIG. 11 is a view for explaining a configuration of the plastic catheter to be used with a guiding wire, and a process of performing pullback scanning, according to an embodiment.

Referring to FIG. 11, the PAI;-EUS system may further include a guiding catheter 290 that surrounds the plastic catheter 220 and includes a guiding catheter injection port 280, and thus may be capable of operating with a guiding wire 270 manufactured as a separate device to be inserted into the guiding catheter injection port 280.

That is, when the guiding catheter 290 which has a dual-lumenal structure over a partial section of the catheter is additionally used as shown in FIG. 11, a liquid medium may be injected through the guiding catheter injection port 280 and also a channel through which the guiding wire 270 may be inserted and guided may be secured. Since the diameter of the plastic catheter 220 is narrower than that of the guiding catheter 290 and the plastic catheter 220 may be physically inserted or retracted, a 3D image may be obtained by changing the position of the scanning tip 250 inside the object to be examined.

Figure 12:
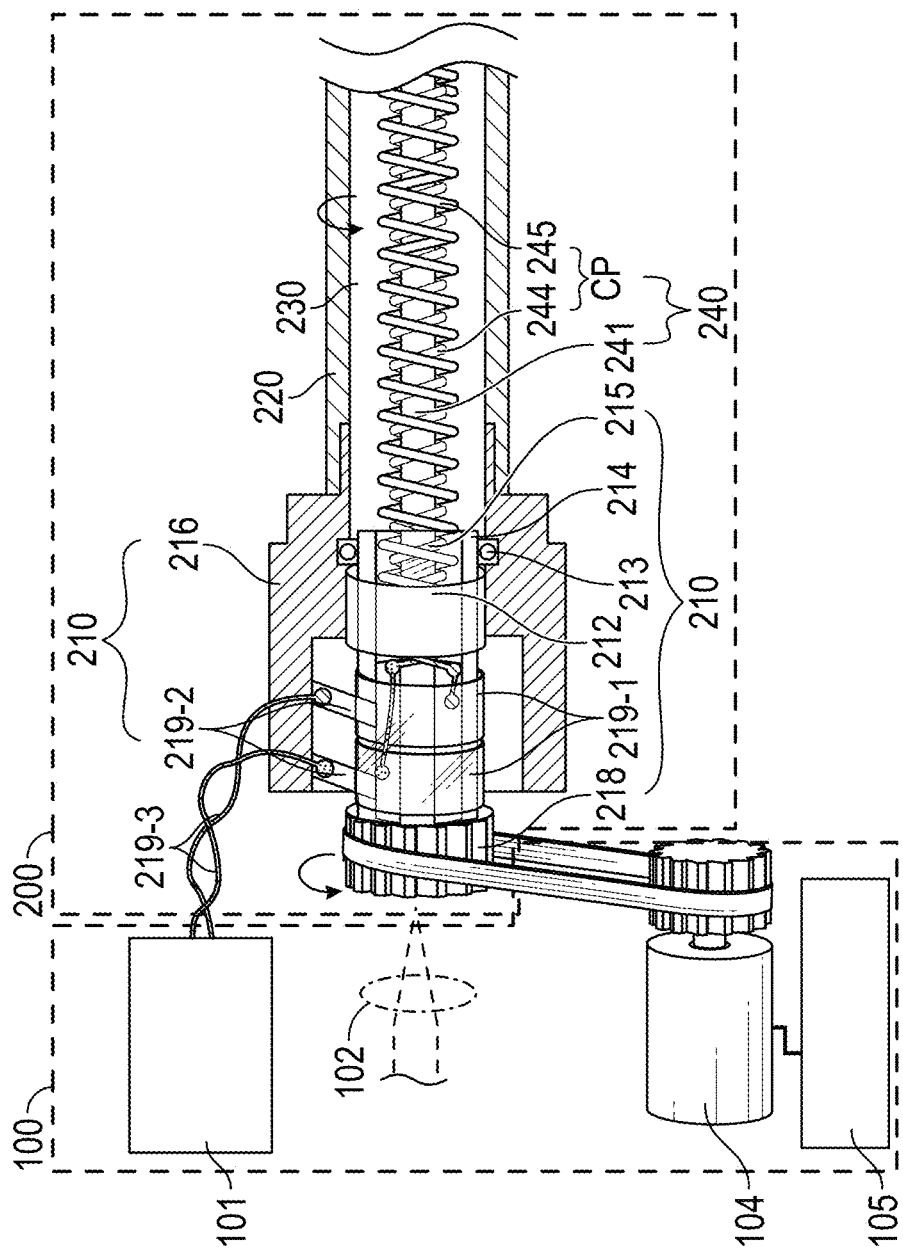
FIG. 12 is a view illustrating configurations of a proximal part and a driving unit, according to another embodiment.

FIG. 12 is a view for explaining a method of transmitting mechanical power and inputting/outputting an electrical signal, which is different from that in FIG. 1, in the probe driving unit 100 and the proximal part 210, according to an embodiment.

In the PAE-EUS system of FIG. 1, the probe driving unit 100 includes the driving gear 103 that is connected to the actuator 104 and rotates, and the proximal part 210 includes the proximal gear 217 that is engaged with the driving gear 103 and rotates following it. That is, the mechanical torque needed to rotate the waveguide assembly 240 is transmitted by the proximal gear 217 directly coupled to the driving gear 103.

However, in the PAE-EUS system of FIG. 12, the probe driving unit 100 may include a driving timing pulley 106 that is connected to the actuator 104 and rotates, and the proximal part 210 may include a proximal timing pulley 218 that is engaged with the driving timing pulley 106 and rotates and may further include a timing belt 107 that transmits the mechanical torque between the driving timing pulley 106 and the proximal timing pulley 218. Accordingly, in this case, the mechanical torque needed to rotate the waveguide assembly 240 is transmitted through the driving timing pulley 106, the proximal timing pulley 218, and the timing belt 107 that connects the driving timing pulley 106 and the proximal timing pulley 218.

Also, in FIGS. 1 and 3, a rotary transformer 211 is mounted in the proximal part 210 and receives an electrical signal generated by the piezoelectric element 251 through the waveguide assembly 240. However, when mechanical noise is not a major part of consideration, the rotary transformer 211 may be replaced with the electrical signal input/output method that uses two slip rings 219-1 and two brushes 219-2 respectively contacting the slip rings 219-1 as shown in FIG. 12. In this case, the two brushes 219-2 are electrically connected to the ultrasonic pulser-receiver 101 through signal cables 219-3.

Although both the proximal timing pulley 218 and the slip rings 219-1 are used in FIG. 12, the proximal timing pulley 218-based torque transmission mechanism may be used along with the concept of rotary transformer 211, or the proximal gear 217-based torque transmission mechanism may be used along with the concept of slip rings 219-1.

While configurations of the PAE-EUS probe 200 and the probe driving unit 100 have been described above, in order to actually perform photoacoustic and ultrasonic dual-mode endoscopic imaging by using the PAE-EUS probe 200 and the probe driving unit 100, other elements such as a light source or a data acquisition (DAQ) system are additionally required, like well-known or general PAT systems.

Figure 13:
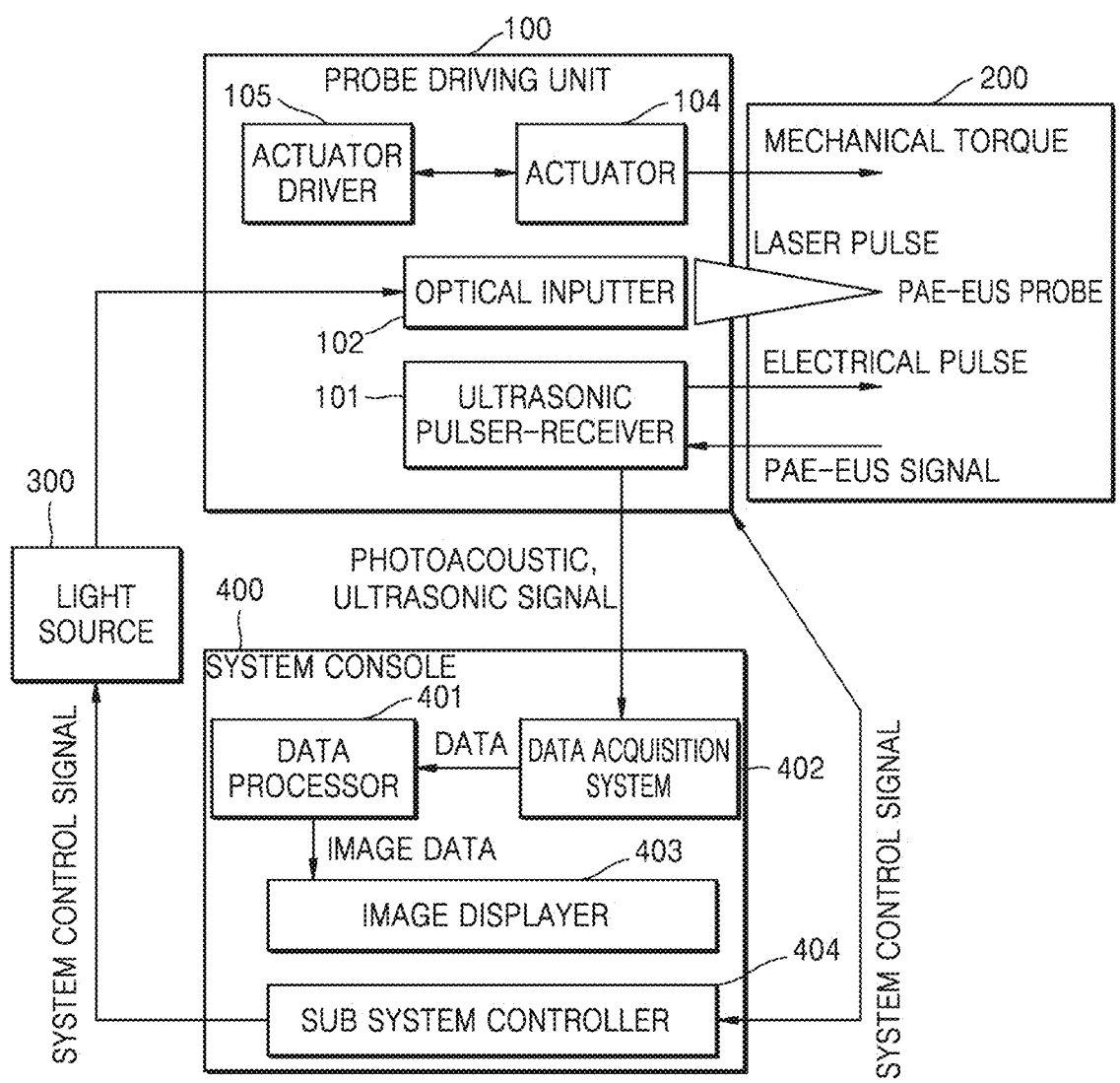
FIG. 13 is a conceptual diagram illustrating a photoacoustic-ultrasonic endoscopic probe, a probe driving unit, and a system console for driving and controlling the probe and the probe driving unit.

FIG. 13 is a conceptual diagram illustrating the PAE-EUS probe 200, the probe driving unit 100, and peripheral systems for driving the PAE-EUS probe 200 and the probe driving unit 100. Representative examples of the peripheral systems include the light source 300 that generates a laser pulse and a system console 400 with which a user may control the entire system.

First, it is preferable that an essential element of the light source 300 is the Q-switched laser system that may be able to provide a laser beam with a very short pulse width. Also, sufficient pulse energy and a sufficient pulse repetition rate should be ensured by the Q-switched laser system to satisfy the purpose of an application required by the endoscopic system. When multi-wavelength photoacoustic imaging is to be simultaneously performed at two or more wavelengths, a plurality of laser systems capable of providing the two or more wavelengths, or a wavelength tunable laser system, may be used.

The system console 400 includes a data acquisition system 402 that receives a photoacoustic signal and an ultrasonic signal amplified and optimized by the ultrasonic pulser-receiver 101 and converts the photoacoustic and ultrasonic signal into a digital signal that may be managed by a computer, a data processor 401 that processes the digital signal into image data, an image displayer 403 that shows the image data to the user, and a subsystem controller 404 that controls a plurality of sub-systems.

Operations of the PAE-EUS probe 200 and the probe driving unit 100 of FIG. 1 will now be explained with reference to FIGS. 1 and 13.

The user inserts the PAE-EUS probe 200 into the object to be examined so that the scanning tip 250 is located in a region of interest, drives the actuator 104 so that the driving gear 103 and the proximal gear 217 engaged with the driving gear 103 start to rotate and accelerate to reach a predetermined speed. For example, when imaging is to be performed at a general video rate, the proximal gear 217 may be accelerated to about 30 Hz.

Once the proximal gear 217 starts to rotate, the hollowed shaft 214 directly connected to the proximal gear 217 also rotates. In this case, the mechanical torque is also directly transmitted to the primary coil unit 211-1 of the rotary transformer 211 engaged with the hollowed shaft 214, the waveguide assembly 240, and the scanning tip 215 located at an end portion of the waveguide assembly 240, and thus the primary coil unit 211-1, the waveguide assembly 240, and the scanning tip 215 also rotate at a predetermined speed. In this case, the ball bearing module 212 of the proximal part 210 provides a mechanical condition in which the hollowed shaft 214 may smoothly rotate in a stable state, and the sealing O-ring 213 prevents the matching liquid medium 230 filled in an inner space of the PAE-EUS probe 200 from leaking out during the physical rotation.

When the mechanical elements interconnected with one another reach the predetermined speed, the actuator driver 105 starts to generate a trigger pulse signal whenever the actuator 104 which is actually the mechanical power source rotates by a predetermined angular step, and a series of imaging sequences for obtaining one-dimensional (1D) photoacoustic and ultrasonic image data (typically, referred to as A-line data) in synchronization with the trigger pulse signal are sequentially and alternately performed in the entire system. That is, every time a trigger pulse signal is generated, ID photoacoustic and ultrasonic data containing depth-resolved information (i.e., radially-resolved information) in a specific direction in which the scanning tip 250 faces is obtained, and pieces of 2D photoacoustic and ultrasonic image data that are spatially coregistered are obtained by continuously and repeatedly performing such a series of processes while the scanning tip 250 rotates. Also, when the series of processes are performed by pushing or pulling the PAE-EUS probe 200, the data needed for producing a 3D image may also be obtained. A trigger pulse used to trigger the imaging sequences may be a transistor-transistor logic (TTL) pulse.

In order to sequentially obtain pieces of 1D photoacoustic and ultrasonic data by using the above method, a trigger pulse train provided by the actuator driver 105 is delivered to the subsystem controller 404, is divided into two different pulse trains with a predetermined time interval therebetween in the subsystem controller 404, and is used for photoacoustic and ultrasonic imaging. The predetermined time interval may be tens of micro seconds (μsec) in general. The reason that 1D photoacoustic and ultrasonic data acquisition moments are triggered separately with a set time interval is because the object to be examined is given time to sufficiently relax in the two photoacoustic and ultrasonic modes that alternately occur. For reference, the prior document 11 discloses that such imaging sequences are actually used.

How 1D photoacoustic and ultrasonic image data are obtained by using a single trigger pulse will now be explained.

First, when a photoacoustic imaging mode for obtaining 1D photoacoustic data starts at a specific time, a laser pulse is first generated by the light source 300, the laser pulse is sent through a separate optical fiber (not shown) to the optical inputter 102, is delivered along the optical fiber 241 provided along the central axis of the waveguide assembly 240 from the proximal part 210 to the scanning tip 250, and is finally sent through the optical reflector 252 to the object to be examined. When the light source 300 is integrated with the probe driving unit 100, a separate optical fiber for delivering a laser pulse generated by the light source 300 to the probe driving unit 100 is not required.

When a laser beam is delivered into the object to be examined, photoacoustic waves are immediately induced, and a part of the induced photoacoustic waves propagate to the piezoelectric element 251 and they are converted into an electrical signal. The electrical signal is guided through the electromagnetic waveguide formed by the first conductive path 242 and the second conductive path 243 of the waveguide assembly 240 and through the rotary transformer 211 of the proximal part 210 to the ultrasonic pulser-receiver 101 of the probe driving unit 100. Although the ultrasonic pulser-receiver 101 receives a photoacoustic signal detected and electrically converted by the piezoelectric element 251, the ultrasonic pulser-receiver 101 may also provide an electrical pulse to the piezoelectric element 251 so that the piezoelectric element 251 emits an ultrasonic pulse to the object to be examined, and may receive the ultrasonic echo signal detected by the piezoelectric element 251.

In addition, the ultrasonic pulser-receiver 101 may perform a signal conditioning to amplify a signal and filter only an appropriate frequency band. Optimized signals are then sent to the data acquisition system 402, are processed by the data processor 401 of the system console 400, and are stored temporarily or for a long time.

When a series of processes of obtaining 1D photoacoustic data end, an ultrasonic imaging mode for obtaining 1D ultrasonic data with a preset time interval starts. The scanning tip 250 may rotate a little during the preset time interval.

When this process starts, a very short electrical pulse is generated in the ultrasonic pulser-receiver 101, is delivered through the rotary transformer 211 and the first conductive path 242 and the second conductive path 243 of the waveguide assembly 240 to the piezoelectric element 251, and is converted into an ultrasonic pulse. The ultrasonic pulse propagates to the object to be examined in a similar manner to that in a typical ultrasonic imaging process, a part of the ultrasonic pulse is reflected and returned and is detected by the same piezoelectric element 251 that has emitted the ultrasonic pulse, and the received part of the ultrasonic pulse is converted into an electrical signal. Next, the electrical signal is further delivered through the first conductive path 242 and the second conductive path 243 of the waveguide assembly 240 to the rotary transformer 211 and is finally received and amplified by the ultrasonic pulser-receiver 101 in reverse order. The amplified ultrasonic signal is sent to the data acquisition system 402, is processed by the data processor 401 of the system console 400, and is stored temporarily or for a long time, like the photoacoustic signal.

Once 1D photoacoustic and ultrasonic image data are obtained according to the above method for a predetermined time e.g., while the scanning tip 250 completely rotates one time, in general), pieces of related data are processed by the data processor 401 and are displayed to the user through the image displayer 403.

The main objective of the present disclosure is for it to be used in a photoacoustic and ultrasonic dual imaging mode. But, if the optical fiber 241 of the waveguide assembly 240 is an optical fiber having a double cladding structure or a single-mode optical fiber, and also peripheral systems elements are configured as shown in FIG. 14, a photoacoustic-ultrasonic-OCT triple imaging mode may also be performed.

Figure 14:
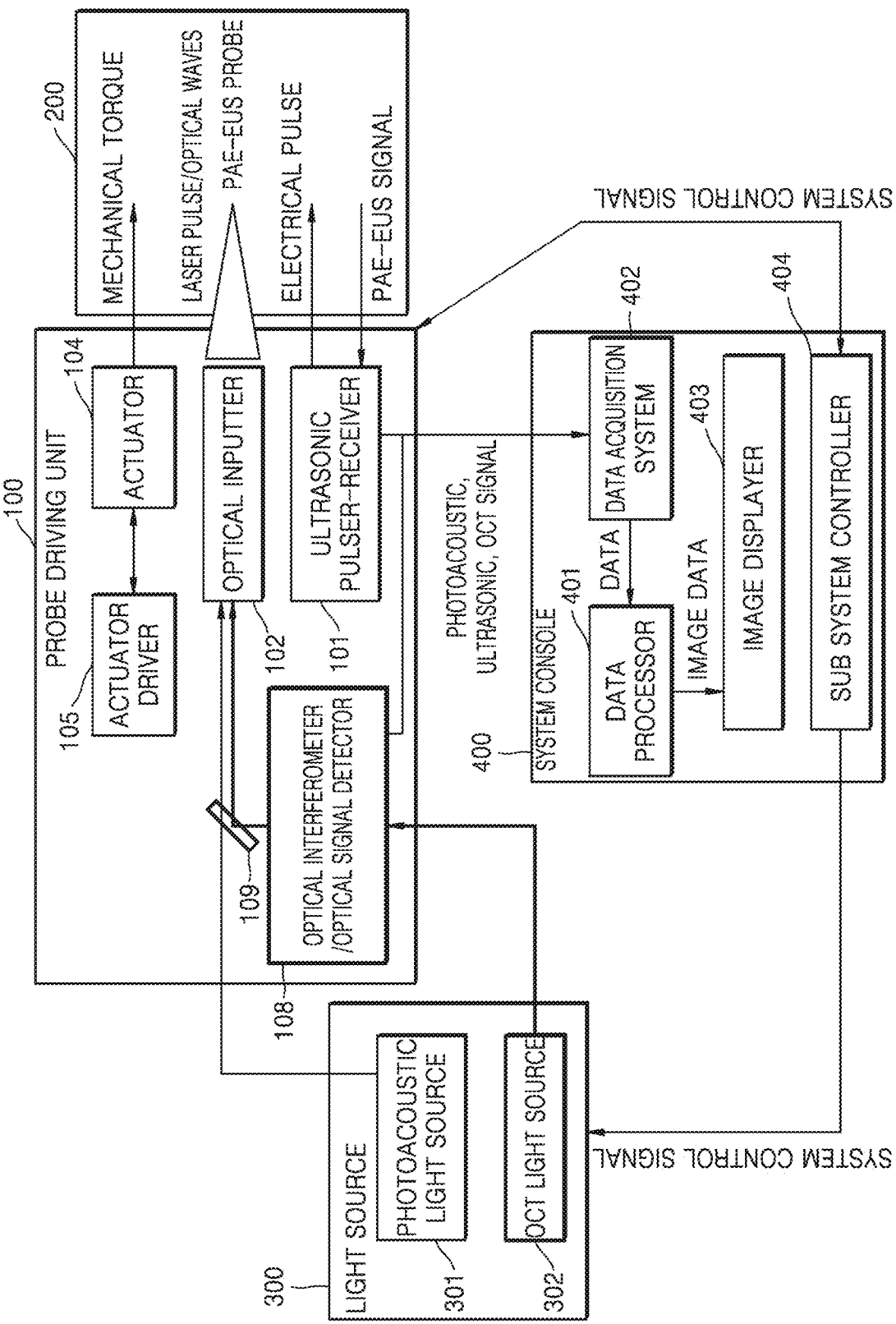
FIG. 14 is a conceptual diagram illustrating system elements for implementing a photoacoustic-ultrasonic-optical coherence tomography (OCT) triple imaging mode, and a connection relationship among the system elements.

FIG. 14 is a conceptual diagram illustrating system elements for implementing a photoacoustic-ultrasonic-OCT triple imaging mode, and a connection relationship among the system elements, Referring to FIG. 14, a photoacoustic-ultrasonic-OCT imaging system according to an embodiment includes an OCT light source 302 for providing optical waves for OCT imaging to the optical fiber 241. A biggest difference between FIGS. 13 and 14 is internal configurations of the light source 300 and the probe driving unit 100. First, the OCT light source 302, e.g., a swept source, is added to the light source 300 in order to perform OCT. For reference, the term 'added' means the addition of a function and it does not mean that a physically separate unit or apparatus has to be added. For example, a single light source may simultaneously provide the optical waves needed for photoacoustic imaging and OCT imaging. In FIG. 14, besides the OCT light source 302, an optical interferometer/optical signal detector 108 that is typically used in an OCT imaging system may be provided in the probe driving unit 100, may receive optical waves from the OCT light source 302, and may additionally perform OCT imaging. In order to effectively deliver the laser light received from the photoacoustic light source 301 and the optical waves received from the OCT light source 302 to the PAE-EUS probe 200, a beam combiner 109 may also be provided in front of the optical inputter 102.

The photoacoustic-ultrasonic-OCT images that are spatially coregistered may be obtained by sequentially starting 1D photoacoustic, ultrasonic, and OCT imaging modes while the scanning tip 250 rotates in a manner similar to that described above.

A method of obtaining photoacoustic, ultrasonic, and OCT image information by using the endoscopic system of the present disclosure has been described. However, if necessary, a system for obtaining only some of image information from among the photoacoustic, ultrasonic, and OCT image information may be implemented. In configurations and arrangements of detailed system elements, e.g., the probe driving unit 100, the light source 300, and the system console 400 of FIGS. 13 and 14, some elements may be integrated as one physical unit if necessary, and positions of sub-systems in the elements may be appropriately changed. For example, the light source 300, the probe driving unit 100, and the system console 400 may be integrally formed, and the OCT light source 302 may be moved to be located inside the probe driving unit 100.

The present disclosure may provide a method of solving the fastidious problems related to the wiring of the optical fiber 241 and an electrical signal line, and inputting/outputting of optical waves and electrical signals in the proximal part 210, which have been very significant problems in the PAE system that operates based on the single-element ultrasonic transducer-based proximal actuation mechanism, by using the inventive principles and structures of the waveguide assembly 240 and the rotary optical and electromagnetic coupler including the optical inputter 102, the optical fiber 241, and the rotary transformer 211.

The key requirement of a PAE system that uses the proximal actuation-based rotation scanning mechanism is that an optical fiber for delivering laser light and an electrical conductive path for transmitting/receiving an electrical signal has to be formed in a predetermined rotating body (i.e., a torque coil). But, existing inventions including Prior Document 4 have problems in that, since the optical fiber and the electrical path are simply arranged in a parallel structure inside the torque coil, uniform mechanical torque cannot be transmitted from the proximal part to the distal end of an imaging probe. That is, in a PAE system that uses the proximal actuation-based rotation scanning mechanism, the flexible probe section that is inserted into an objet to be examined is a very important path through which not only the light energy and the electrical signal but also the mechanical torque needed for a rotational scanning are transmitted. However, the prior inventions fail to provide a method of solving the problems.

On the other hand, the present disclosure provides a structure and an economical implementation method that may effectively deliver both light energy and an electrical signal, without using an electrical signal line that is typically used, by using, for example, the conductive path CP including the first and second conductive paths 242 and 243 which are all coaxially configured.

Accordingly, when a PAE system is implemented based on the present disclosure, since the PAE-EUS probe 200 has a complete rotational symmetric structure, the PAE-EUS probe 200 may have a flexibility and rotation scanning uniformity that are much better than those of similar existing PAE probes, and thereby NURD problems are effectively solved. Also, the PAE-EUS probe 200 is hardly affected by an electromagnetic interference noise present in an external environment, and a signal-to-noise ratio is greatly increased. Accordingly, the PAE-EUS probe 200 may be prevented from being severely twisted or kinked when an insertion depth is large (that is, when the PAE-EUS probe 200 is long) and a curvature is large, thereby improving image quality and greatly extending a lifetime of the PAE-EUS probe 200. The PAE-EUS probe 200 may be more easily inserted into the instrument channel of a video endoscope currently used in clinics.

In the present disclosure, detailed configurations for providing the plastic catheter 220 outside a rotating body, filling the matching liquid medium 230 inside the plastic catheter 220, and finally sealing the plastic catheter 220 near the base frame 216, all of which however have not been achieved concurrently in the prior inventions, have been provided for the first time. Also, a method of configuring the rotary optical and electromagnetic coupler including the optical inputter 102, the optical fiber 241, and the rotary transformer 211, so that an electrical signal can be effectively exchanged via the rotary transformer 211 as well as a laser beans via the rotary optical coupler formed in the proximal part 210, and a method of implementing a photoacoustic-ultrasonic-OCT triple imaging based on the proposed key design concept are provided.

According to an embodiment of the present disclosure including an optical fiber and a conductive path that is coaxial with the optical fiber, since a probe has a complete rotational symmetric structure, the probe may have a flexibility and rotation scanning uniformity that are much better than those of similar existing PAE probes, thereby solving NURD problems. However, the scope of the present disclosure is not limited by the effect.

While one or more embodiments have been described with reference to the figures, it will be understood by those of ordinary skill in the art that various changes in form and details may be made therein without departing from the spirit and scope of the disclosure as defined by the following claims.

What is claimed is:

1. A photoacoustic-ultrasonic endoscope comprising a probe operatively coupleable to a probe driving unit, the probe comprising:
    a rotatable, optical and electromagnetic rotary waveguide assembly including:
        an optical fiber; and
        a conductive path including a first conductor and a second conductor, the first conductor defining a first conductive path, the second conductor defining a second conductive path, the second conductor being insulated from the first conductor;
    a scanning tip located at a distal end of the optical and electromagnetic rotary waveguide assembly and configured to transmit a laser beam to an object to be examined and detect a photoacoustic signal or an ultrasonic signal received from the object to be examined;
    an outer plastic catheter positioned exteriorly of the optical and electromagnetic rotary waveguide assembly and the scanning tip;
    a proximal part electrically connected to the conductive path, the proximal part being configured to receive mechanical torque from the probe driving unit, the proximal part including:
        a shaft configured to deliver the mechanical torque to the optical and electromagnetic rotary waveguide assembly;
        a base frame connected to the outer plastic catheter, the base frame physically surrounding the shaft, an inner surface of the base frame surrounding an outer surface of the shaft; and
        a sealing O-ring interposed between the shaft and the base frame at a longitudinally fixed position relative to the shaft and the base frame, the sealing O-ring directly contacting both the outer surface of the shaft and the inner surface of the base frame; and
    a rotary transformer, the rotary transformer including:
        a primary coil unit electrically connected to the conductive path, the primary coil unit being connected to the shaft to rotate along with the optical and electromagnetic rotary waveguide assembly, a central axis of the primary coil unit coinciding with a longitudinal axis defined by the optical fiber; and
        a secondary coil unit arranged such that a central axis of the secondary coil unit coincides with both the central axis of the primary coil unit and the longitudinal axis defined by the optical fiber, the secondary coil unit being next to the primary coil unit, and the secondary coil unit is connected to the base frame that does not rotate while the primary coil unit rotates due to a ball bearing module between the shaft and the base frame.

2. The photoacoustic-ultrasonic endoscope of claim 1, wherein the optical fiber guides the laser beam from the proximal part to the scanning tip.

3. The photoacoustic-ultrasonic endoscope of claim 1, wherein the first conductor and the second conductor guide an electrical signal converted from the photoacoustic signal by a piezoelectric element of the scanning tip, from the scanning tip to the proximal part, and the first conductor and the second conductor transmit mechanical torque from the probe driving unit along with the optical fiber.

4. The photoacoustic-ultrasonic endoscope of claim 1, wherein at least one of the first conductor and the second conductor comprises a torque coil set formed as a coil exteriorly of the optical fiber.

5. The photoacoustic-ultrasonic endoscope of claim 1, wherein the rotary waveguide assembly comprises an insulating coating layer between the first conductor and the second conductor.

6. The photoacoustic-ultrasonic endoscope of claim 1, wherein the optical fiber comprises a first cladding configured to propagate light waves and a second cladding surrounding the first cladding.

7. The photoacoustic-ultrasonic endoscope of claim 1, wherein the first conductor comprises a tubular or coiled portion coaxially arranged with and surrounding the optical fiber, and the second conductor comprises a tubular or coiled portion coaxially arranged with and surrounding both the optical fiber and the first conductor.

8. The photoacoustic-ultrasonic endoscope of claim 1, further comprising a mesh reinforcement inside the plastic catheter.

9. The photoacoustic-ultrasonic endoscope of claim 1, wherein the probe further comprises an injection port.

10. The photoacoustic-ultrasonic endoscope of claim 1, further comprising:

a guiding catheter surrounding the plastic catheter and comprising a guiding catheter injection port; and a guiding wire inserted into the guiding catheter injection port.

11. The photoacoustic-ultrasonic endoscope of claim 1, further comprising a light source for optical coherence tomography (OCT), wherein the light source is configured to supply light waves for OCT to the optical fiber.

12. The photoacoustic-ultrasonic endoscope of claim 1, wherein the first conductor has a U shape in a cross-sectional view perpendicular to the longitudinal axis defined by the optical fiber to partially surround the optical fiber, and the second conductor has an inverted-U shape in the cross-sectional view perpendicular to the longitudinal axis to partially surround the optical fiber.

13. The photoacoustic-ultrasonic endoscope of claim 1,
wherein the first conductor is formed as a first torque coil, and the second conductor is formed as a second torque coil.

14. The photoacoustic-ultrasonic endoscope of claim 13, wherein the first torque coil is one torque coil of a multi-layer first torque coil set, and wherein the second torque coil is one torque coil of a multi-layer second torque coil set.

15. The photoacoustic-ultrasonic endoscope of claim 13, wherein at least one of the first torque coil and the second torque coil is coated with a material providing electrical conductivity.

\* \* \* \* \*